(12) United States Patent
Orbach et al.

(10) Patent No.: US 10,413,602 B2
(45) Date of Patent: *Sep. 17, 2019

(54) FUNGAL IMMUNOGENS AND RELATED MATERIALS AND METHODS

(71) Applicant: Arizona Board of Regents on Behalf of the University of Arizona, Tucson, AZ (US)

(72) Inventors: Marc J. Orbach, Tucson, AZ (US); Lisa F. Shubitz, Tucson, AZ (US); Hema P. Narra, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/841,921

(22) Filed: Dec. 14, 2017

(65) Prior Publication Data

US 2018/0117132 A1    May 3, 2018

Related U.S. Application Data

(63) Continuation of application No. 14/774,504, filed as application No. PCT/US2014/023606 on Mar. 11, 2014, now Pat. No. 9,884,097.

(60) Provisional application No. 61/776,770, filed on Mar. 11, 2013, provisional application No. 61/777,845, filed on Mar. 12, 2013.

(51) Int. Cl.
*A01N 63/00* (2006.01)
*A61K 39/00* (2006.01)
*A01N 63/04* (2006.01)
*A61K 36/06* (2006.01)
*C12N 15/113* (2010.01)

(52) U.S. Cl.
CPC .......... *A61K 39/0002* (2013.01); *A01N 63/04* (2013.01); *A61K 36/06* (2013.01); *C12N 15/113* (2013.01); *A61K 2039/522* (2013.01); *A61K 2039/54* (2013.01); *A61K 2039/543* (2013.01); *A61K 2039/545* (2013.01); *A61K 2039/55* (2013.01); *A61K 2039/552* (2013.01); *C12N 2310/14* (2013.01)

(58) Field of Classification Search
CPC .................................................... A61K 39/002
See application file for complete search history.

(56) References Cited

U.S. PATENT DOCUMENTS 9,884,097 B2 * 2/2018 Orbach .................. A61K 36/06

\* cited by examiner

*Primary Examiner* — Albert M Navarro
(74) *Attorney, Agent, or Firm* — MacMillan, Sobanski & Todd, LLC

(57) ABSTRACT

The present disclosure provides immunogenic materials and methods useful for reducing the risk of fungal infections, particularly valley fever. The disclosure also provides assays for identifying compounds useful to treat valley fever, as well as methods for ameliorating the symptoms of valley fever.

22 Claims, 10 Drawing Sheets
(8 of 10 Drawing Sheet(s) Filed in Color)
Specification includes a Sequence Listing.

FUNGAL IMMUNOGENS AND RELATED MATERIALS AND METHODS

CROSS REFERENCE TO RELATED APPLICATIONS

This application is a continuation of U.S. Ser. No. 14/774,504 filed Sep. 10, 2015, now allowed, which claims priority to PCT No. PCT/US2014/023606 filed Mar. 11, 2014, which claims the benefit of U.S. Ser. No. 61/776,770 filed Mar. 11, 2013, and U.S. Ser. No. 61/777,845 filed Mar. 12, 2013, the disclosures of which are incorporated herein by reference.

STATEMENT REGARDING FEDERALLY SPONSORED RESEARCH

This invention was made with government support under Grant No. PO1 AI061310 awarded by the National Institutes of Health (NIH). The government has certain rights in the invention.

REFERENCE TO SEQUENCE LISTING SUBMITTED VIA EFS-WEB

This application is being filed electronically via the USPTO EFS-WEB server, as authorized and set forth in MPEP § 1730 II.B.2(a)(A), and this electronic filing includes an electronically submitted sequence (SEQ ID) listing. The entire content of this sequence listing is herein incorporated by reference for all purposes. The Sequence Listing, filed electronically and identified as 3726_54785_SEQ_LIST_UA12-127, was created on Mar. 7, 2014, is 34,266 kb in size.

| Sequence Listing Brief Descriptions | |
|---|---|
| SEQ ID NO | Brief Description |
| 1 | Reference CPS1 gene product; protein; amino acid sequence |
| 2 | Reference CPS1 genomic DNA; nucleic acid sequence |
| 3-10 | Primers |

BACKGROUND OF INVENTION

*Coccidioides* species (*C. immitis* and *C. posadasii*) are the causative agents of coccidioidomycosis (Valley Fever), an important emerging disease endemic to the southwestern US as well as parts of Mexico and central and South America. Infection begins with inhalation of arthroconidia that initiate the parasitic phase in lungs and can result in a respiratory infection or if not controlled, a more serious disseminated disease.

*Coccidioides* spp. are dimorphic and produce a unique parasitic phase structure, the spherule, via a switch from polar to isotrophic growth with the spherule expanding from a barrel-shaped arthrocondium that is 3-6 μm by 2-4 μm in size to a sphere 80-100 microns in diameter. Internal septation and spore formation results in production of hundreds of endospores that if released can disseminate and reinitiate spherule formation at other places in the body. Most infections are mild and resolve without medical intervention although about 30% of infections cause flu-like symptoms that may take 1-4 months to resolve.

A variety of approaches have been used to understand genes important for the parasitic phase of these and other fungi. These include random mutagenesis, targeted disruption of parasitic phase-specific genes and targeted mutagenesis of genes identified in other pathogens as virulence factors. In addition, expression analyses have been performed to identify phase-specific or phase-induced genes. For *Coccidioides*, both expression analyses and the latter two mutagenesis approaches have been used, resulting in a number of mutants, some of which are altered in virulence. For example, SOWgp and MEP1 have been knocked out and the resulting mutant strains are reduced in virulence.

Over the last 50 years, many approaches to vaccination against coccidioidomycosis have been tried, including whole killed cells, live mutant vaccines that have been modified in virulence, partially purified cellular extracts, and recombinant proteins that were identified by a myriad of both low and high technology methods. To date, killed whole cell vaccines provide the best protection in mice but are not transferable to humans because of intolerable adverse effects and poor efficacy. Recombinant proteins offer the safest approach but have modest efficacy in mice and have not been tried in a higher species.

SUMMARY OF THE INVENTION

Without being held to any particular theory, the inventors have discovered a gene in fungi, which, if disrupted, results in leaky or otherwise more vigorous immune response-provoking variations on the wild type fungus. Further, these cyclic peptide synthase Cps1 analog (CPS1), "CPS1 analog" deletion mutant fungal spores are not virulent; introduction of the immunogens will not result in immunogen-induced pathology in an animal exposed to the immunogen.

The inventors demonstrate herein that CPS1 is essential for virulence in the mouse model of coccidioidomycosis and that pre-infection of mice with a CPS1 mutant strain protects mice against subsequent infection with wild type *Coccidioides*.

The present disclosure therefore provides compositions comprising a fungus having a dysfunctional CPS1 gene product, wherein the composition is avirulent and capable of inducing an immune response in a mammal.

Also provided are such compositions, wherein the dysfunctional CPS1 gene product is a result of a deletion of at least a portion of the CPS1 gene.

Also provided are such compositions, wherein the dysfunctional CPS1 gene product is a result of a deletion in a region of the CPS1 gene selected from the group consisting of: at least about the entire CPS1 gene; at least about the entire DMAP region of the CPS1 gene; at least about an entire AMP binding domain region of the CPS1 gene; a regulatory element of the CPS1 gene; at least the coding sequence of the CPS1 gene; at least about 90% of the CPS1 gene; at least about 80% of the CPS1 gene; at least about 70% of the CPS1 gene; at least about 60% of the CPS1 gene; at least about 50% of the CPS1 gene; at least about 40% of the CPS1 gene; at least about 30% of the CPS1 gene; at least about 20% of the CPS1 gene; at least about 10% of the CPS1 gene.

Also provided are such compositions, wherein the dysfunctional CPS1 gene product is a result of deletion of the entire CPS1 gene.

Also provided are such compositions, wherein the composition is capable of inducing an immune response as a result of secretion of a metabolite or small molecule.

Also provided are such compositions, wherein the composition is capable of inducing an immune response selected from the group consisting of: neutrophil invasion; granuloma formation; resistance to mycosis; and immunity to mycosis.

Also provided are such compositions, wherein the fungus is a *Coccidioides* spp.

Also provided are such compositions, wherein the composition is capable of inducing resistance to coccidioidomycosis (valley fever).

Also provided are such compositions, wherein the composition is capable of inducing immunity to coccidioidomycosis (valley fever).

Also provided are such compositions, wherein the fungal cell is selected from the group consisting of: *Coccidioides immitis; Coccidioides posadasii; Aspergillus fumigatus; Aspergillus flavus; Histoplasma capsulatum; Blastomyces dermatitidis; Cryptococcus neoformans; Cryptococcus laurentii* and *Cryptococcus albidus; Cryptococcus gattii; Candida albicans; Candida glabrata; Saccharomyces boulardii; Candida tropicalis; Candida krusei;* and *Candida parapsilosis*.

Also provided are such compositions, wherein the fungal cell is *Magnaporthe oryzae*.

Also provided are such compositions, which are formulated as a vaccine.

Also provided are such compositions, wherein the composition comprises further avirulence protection means.

Also provided are such compositions, wherein the further avirulence protection means is selected from the group consisting of; amino acid biosynthesis knockout; truncation; aging; modification; killing; formulation; resistance to reversion to wild type; and fusion.

Also provided are such compositions, which is a mammalian immunogen.

Also provided are such compositions, which is a human immunogen.

The present disclosure also provides methods of preparing a pharmaceutical composition for passive immunization of an individual in need of immunization comprising: mixing a composition herein with a suitable excipient or carrier, thereby forming a pharmaceutical composition.

The present invention also provides methods of eliciting an immune response in a mammal comprising: administering to a mammal a pharmaceutically-effective dose of a composition herein.

Also provided are such methods wherein the composition is administered by injection.

Also provided are such methods wherein the composition is administered intranasally.

Also provided are such methods wherein the pharmaceutical composition is formulated for subcutaneous, intramuscular, and/or intraperitoneal administration.

Also provided are such methods wherein the pharmaceutical composition is formulated for intranasal administration.

Also provided are such methods wherein the fungal virulence is attenuated or eliminated in any mammal susceptible to the fungus.

Also provided are such methods wherein the mammalian subject is selected from the group consisting of: laboratory animal; companion animal; draft animal; meat animal; zoo animal; and human.

Also provided are such methods wherein the subject is a mammal selected from the group consisting of: cat; dog; horse; bovine; camelids; and human.

Also provided are such methods wherein the dose of composition administered is selected from the group consisting of: at least about 500 spores of the composition; at least about 1,000 spores of the composition; at least about 10,000 spores of the composition; at least about 20,000 spores of the composition; at least about 30,000 spores of the composition; at least about 40,000 spores of the composition; at least about 50,000 spores of the composition; at least about 60,000 spores of the composition; at least about 70,000 spores of the composition; at least about 80,000 spores of the composition; at least about 90,000 spores of the composition; at least about 100,000 spores of the composition; at least about 150,000 spores of the composition; at least about 200,000 spores of the composition; at least about 300,000 spores; at least about 500,000 spores.

Also provided are such methods which further comprise administering at least a second subsequent dose of the composition to the mammal.

Also provided are such methods wherein the at least second subsequent dose is administered at a time interval selected from the group consisting of: approximately one week after the first dose; approximately two weeks after the first dose; approximately three weeks after the first dose; approximately four weeks after the first dose; approximately five weeks after the first dose; approximately six weeks after the first dose; approximately seven weeks after the first dose; and approximately eight weeks after the first dose.

The present disclosure also provides methods to reduce the pathogenic effects of *Coccidioides*, comprising administering a siRNA complementary to CPS1 mRNA transcripts.

The present disclosure also provides methods for screening compounds useful to treat coccidioidomycosis, comprising expressing CPS1 in a test model, introducing a test compound to the test model, and identifying those compounds which disrupt the function of CPS1 gene product as useful to treat coccidiodiodomycosis.

BRIEF DESCRIPTION OF THE FIGURES

The patent or application file may contain one or more drawings executed in color and/or one or more photographs. Copies of this patent or patent application publication with color drawing(s) and/or photograph(s) will be provided by the Patent Office upon request and payment of the necessary fee.

FIG. 3A. NSG mice (NOD-SCID—No lymphocytic origin cells, no NK cells) were challenged with 10,000 spores intranasally (IN) of Δcps1 and sacrificed for histopathology. Spherules are occasional, thin-walled, and irregularly shaped. FIG. 3B. WT spherules in C57BL/6 mice after infection with 50 spores showing thick walls and very round shape of normal spherules.

FIG. 4A. WT Silveira *C. posadasii* strain, day 3, C57BL/6. FIGS. 4B-4-D. Δcps1 *C. posadasii*-strain day 3.

FIG. 5A. 10× imagine of very few spherules observed in NSG mice. FIG. 5B. 40× image of the area represented by the circle in A.

FIG. 9A. Low magnification view. FIG. 9B. Larger magnification view FIG. 10. H&E staining of Δcps1 spherule on day 3. High magnification shows collapsing and degenerating spherule wall of the mutant strain with abundant host inflammation surrounding it and inside it.

FIG. 13A. H/E staining, low magnification FIG. 13B. *Coccidioides*-specific staining, higher magnification.

DETAILED DESCRIPTION OF THE INVENTION

Figure 1:
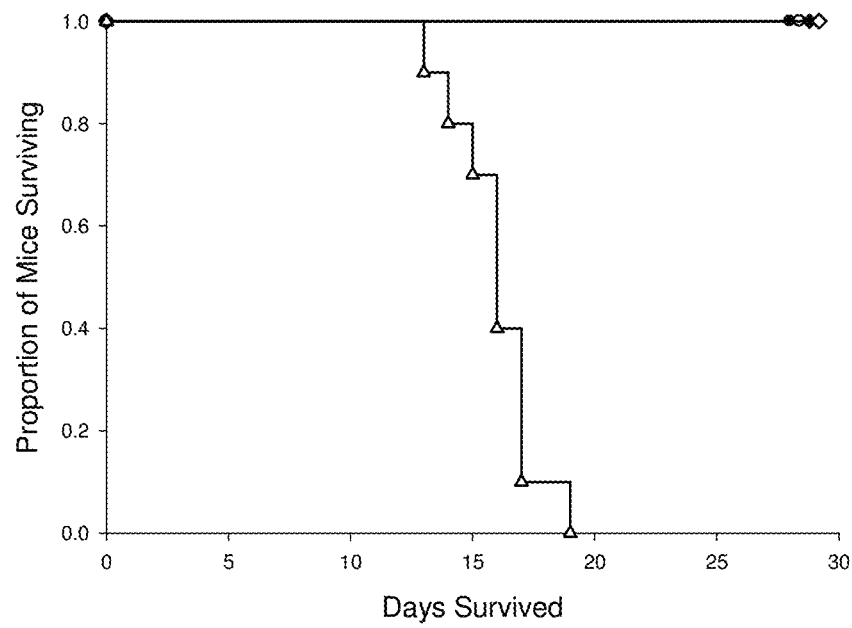
FIG. 1. C57BL/6 mice challenged with intranasal doses of Δcps1 strain ranging from 50-4400 spores. All survived infection for 28 days, while 100% of mice challenged with WT *C. posadasii* succumbed by day 18 (p<0.01). Closed circles, open circles, closed diamonds, and open diamonds are CPS1 deletion mutants (Δcps1) with spore doses of 50, 211, 810, and 4400, respectively; open triangles: WT, 59 spores.
Figure 2:
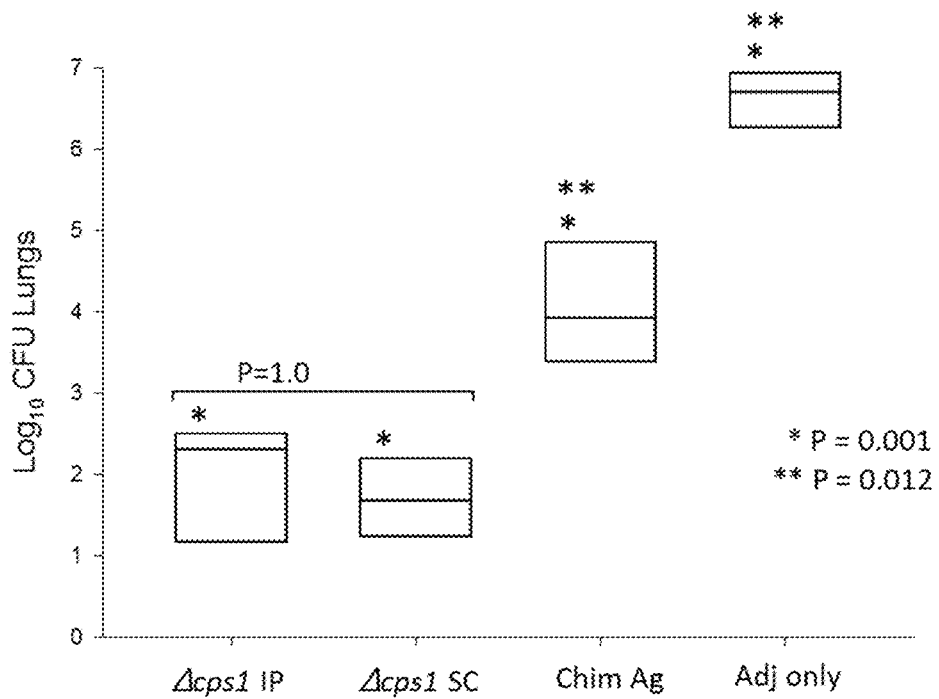
FIG. 2. Protection of C57BL/6 mice by live vaccination with Δcps1 strain. Quantitative total lung colony forming units (CFU) 14 days following challenge with 90 spores of WT *C. posadasii* were significantly reduced in mice vaccinated with ΔCPS1 strain intraperitoneally (Δcps1 IP) or subcutaneously (Δcps1 SC) compared to the positive control chimeric Ag (Chim Ag) or adjuvant alone (Adj only) (P=0.001).

The inventors designed and characterized a *Coccidioides* cyclic peptide synthase Cps1 (herein referred to as CPS1) mutant and determined its usefulness as a potential immune response-provoking agent for protection against coccidioidomycosis (Valley fever).

The inventors constructed a targeted gene-replacement strain of *C. posadasii* strain Silveira deleting the gene CIMG_03303.3 (misannotated as CPSG_02657.2 and CPSG_02658.2 in Silveira) using Agrobacterium-mediated transformation. This gene encodes an 1879 amino acid protein that exhibits 78% similarity to *C. heterostrophus* CPS1 and contains two conserved AMP-binding domains and an N-terminal DMAP1 binding domain, herein referred to as cyclic peptide synthase Cps1 (CPS1).

The hyphal growth rate of the deletion mutant CPS1 (Δcps1) strain was somewhat reduced compared to Silveira at 24° C., but there was no significant difference at 37° C. In vitro analysis of the parasitic phase indicated that the Δcps1 mutant is able to form spherules although they are reduced in size relative to Silveira.

Surprisingly, the inventors discovered that when Δcps1 arthroconidia were introduced into susceptible C57BL/6 mice via intranasal inoculation, no disease occurred, demonstrating it is avirulent and that Cps1 protein is a virulence factor in *Coccidioides*. For C57BL/6 mice, 50 arthroconidia are a lethal dose, while for Δcps1 strains, even when mice were inoculated with 5000 spores, no signs of disease were observed; and all mice remained healthy. In only one of the 20 mice inoculated with >800 Δcps1 spores, was any *Coccidioides* recovered, a single colony from the lung of that mouse. The inventors herein describe that Δcps1 fungi can induce protection against further infection and act as a live vaccine.

As exemplified herein, the inventors injected C57BL/6 mice either intraperitoneal or subcutaneously with 50,000 Δcps1 spores and boosted with the same amount after two weeks. Four weeks later, the mice were challenged intranasally with 90 spores of *Coccidioides* strain Silveira.

The control mice all developed disease, but the inventors show that the Δcps1 mutant provides complete protection against infection, with no sign of disease in infected mouse lungs or other organs.

Interestingly, at the site of injection of Δcps1 arthroconidia, all mice had evidence of granulomatous lesions, indicating local reproduction of the mutant. The present disclosure therefore provides, inter alia, mutant strains of fungus as live vaccines against fungal pathologies, including coccidioidomycosis.

Further, via metabolite analysis of WT and the Δcps1 mutant, the inventors have observed small molecule differences between the strains.

The small metabolite product and the gene are targets for drug therapeutics. Because this gene is conserved among fungi, it is a general target for therapeutics in treatment of fungal diseases.

Previous efforts at development of fungal vaccines were based on either whole cell extracts, partially purified extracts or recombinant proteins. None of the previous attempts produced the protection seen with the present mutant strains.

Unlike other live attenuated vaccines, Cps1 may be part of an enzyme complex that produces one or more small molecules that may have a role in virulence. The invention of the CPS1 mutant could lead to a vaccine or to targets for treatment either through binding of the small molecules involved in virulence or by binding or disrupting the protein involved in making the small molecules required for virulence.

Definitions

*Coccidioides* cyclic peptide synthase Cps1, herein referred to as Cps1, is a protein encoded by a CPS1 gene product and CPS1 mRNA, and may encode either wild type or a mutant. A wild type or mutant CPS1 gene product will encode for a Cps1 protein.

The term "dysfunctional," "non-functional," "inactivated," or "inactivation" when referring to a gene or a protein means that the known normal function or activity of the gene or protein has been eliminated or highly diminished. For example, inactivation of CPS1 can be effected by inactivating the CPS1 gene. Inactivation which renders the gene or protein dysfunctional includes such methods as deletions, mutations, substitutions, interruptions or insertions in the nucleic acid gene sequence.

General techniques of genetic recombination, including vector construction, transformation, selection of transformants, host cell expression, etc., are further described in Maniatis et al, 1989, Molecular Cloning, A Laboratory Manual, Cold Spring Harbor Laboratory Press, Cold Spring Harbor, N.Y.; Ausubel et al., 1989, Current Protocols in Molecular Biology, Greene Publishing Associates & Wiley Interscience, N.Y.; Innis et al. (eds), 1995, PCR Strategies, Academic Press, Inc., San Diego, Calif.; and Erlich (ed), 1992, PCR Technology, Oxford University Press, New York. *Agrobacterium* transformation and replacement of *Coccidioides* genes was as described in Abuodeh et al. 2000, Genetic Transformation of *Coccidioides immitis* facilitated by *Agrobacterium tumefaciens*. Journal of Infectious Diseases, 181:2106-2110 and Kellner et al., 2005, *Coccidioides posadasii* contains a single 1,3-beta-glucan synthase gene that appears to be essential for growth, Eukaryotic Cell, 4:111-120.

As used herein, a "therapeutically effective amount" means a quantity of a specified pharmaceutical or therapeutic compound or composition sufficient to achieve a desired effect in a subject, or in a cell, being treated with the compound or composition. The effective amount of the agent will be dependent on several factors, including, but not limited to, the subject or cells being treated, and the manner of administration of the therapeutic composition.

As is conventional in the art, the term "attenuated" refers to a cell, culture, or strain of fungus (e.g. *Coccidioides* spp.) exhibiting a detectable reduction in infectivity or virulence in vitro and/or in vivo as compared to that of the parent strain of the fungus from which the attenuated cell, culture, or strain is derived. Reduction in virulence encompasses any detectable decrease in any attribute of virulence, including infectivity in vitro and/or in vivo, or any decrease in the severity or rate of progression of any clinical symptom or condition associated with infection.

The term "avirulent", as used herein, does not mean that a microbe of that genus or species cannot ever function as a pathogen, but that the particular microbe being used is avirulent with respect to the particular animal being treated. The microbe may belong to a genus or even a species that is normally pathogenic but must belong to a strain that is avirulent. The microbe may also be modified genetically or through avirulence protection means to make the microbe avirulent. Examples of avirulent means include, but are not limited to, genetic engineering to knock out genes required for virulence, amino acid biosynthesis knockout, truncation of the viral genome, aging, killing, formulation, resistance to reversion to wild type, and fusion. "Pathogenic," as used herein, means capable of causing disease or impairing normal physiological functioning. An "avirulent strain" is incapable of inducing the full set of symptoms of the disease that is normally associated with its virulent pathogenic counterpart. The term "microbes," as used herein, includes bacteria, protozoa, and fungi. Derivatives of avirulent *Coccidioides* spp. are also contemplated to be within the scope of this disclosure. By "derivative" it is meant sexually or asexually derived progeny and mutants of the avirulent strains including single or multiple base substitutions, deletions, insertions or inversions which retain the inability to produce functional Cps1 protein. For example, the *Coccidioides posadasii* Silveira strain that has a deletion of the CPS1 gene described herein.

The term "immunogen," "immunogens," "antigen," or "antigens" means a material that can induce an immune response and is therefore antigenic. By "immune response" means any reaction by the immune system. These reactions include the alteration in the activity of an organism's immune system in response to an antigen and may involve, for example, antibody production, induction of cell-mediated immunity, complement activation or development of immunological tolerance. Immune response to antigens is well studied and widely reported. A survey of immunology is given in Barrett, James, T., Textbook of Immunology: Fourth Edition, C. V. Mosby Co., St. Louis, Mo. (1983). More specifically, the present disclosure provides a live, attenuated fungus (e.g. *Coccidioides* spp.) that can be used as an immunogenic composition or a vaccine. It will be appreciated that the attenuated fungus contains a dysfunctional CPS1 gene.

"Vaccine," as used herein, means an agent used to stimulate the immune system of a living organism so that protection against future harm is provided. "Immunization" refers to the process of inducing a continuing high level of antibody and/or cellular immune response in which T-lymphocytes can either kill a pathogen and/or activate other cells (e.g., phagocytes) to do so in an organism, which is directed against a pathogen or antigen to which the organism has been previously exposed.

The term "adjuvant" is intended to mean a composition with the ability to enhance an immune response to an antigen generally by being delivered with the antigen at or near the site of the antigen. Ability to increase an immune response is manifested by an increase in immune mediated protection. Enhancement of humoral immunity can be determined by, for example, an increase in the titer of antibody raised to the antigen. Enhancement of cellular immunity can be measured by, for example, a positive skin test, cytotoxic T-cell assay, ELISPOT assay for IFN-gamma or IL-2. Adjuvants are well known in the art. Exemplary adjuvants include, for example, Freud's complete adjuvant, Freud's incomplete adjuvant, aluminum adjuvants, MF59 and QS21.

As used herein, "inhibit," "inhibiting," or "inhibition" includes any measurable or reproducible reduction in the infectivity of a fungus in the subject. "Reduction in infectivity" means the ability of the subject to prevent or limit the spread of the fungus in tissues or organs exposed to or infected by the fungus. Furthermore, "amelioration," "protection," "prevention," and "treatment" mean any measurable or reproducible reduction, prevention, or removal of any of the symptoms associated with fungal infectivity, and particularly, the prevention, or amelioration of infection and resultant pathology itself.

As used herein, "subject" means a patient or individual having symptoms of, or at risk for, fungal infection, coccidioidomycosis, or other malignancy. A subject may be human or non-human and may include, for example, laboratory animal, companion animal; draft animal, meat animal, zoo animal, and human. The subjects may include either adults or juveniles (e.g., children). Moreover, subject may mean any living organism, preferably a mammal (e.g., human or non-human) that may benefit from the administration of compositions contemplated herein.

Compositions

The current disclosure provides compositions comprising a fungus having a dysfunctional CPS1 gene product. The compositions may be formulated as an ingredient in a pharmaceutical composition, and this formulation can aid in administration of the composition. The compositions may routinely contain pharmaceutically acceptable concentrations of salts, buffering agents, preservatives and various compatible carriers or diluents. For all forms of delivery, the vectors may be formulated in a physiological salt solution. In one embodiment, the composition is a vaccine.

The preferred formulations of the composition may depend on the method of administration of the composition. It is contemplated that the composition will include one or more conventional pharmaceutically acceptable carriers, adjuvants, other immune-response enhancers, and/or vehicles (collectively referred to as "excipients"). Such excipients are generally selected to be compatible with the active ingredient(s) in the composition. Use of excipients is generally known to those skilled in the art. Suitable pharmaceutical carriers, excipients, adjuvants and the preparation of dosage forms are described in, for example, Remington's Pharmaceutical Sciences, 17th Edition, (Gennaro, Ed., Mack Publishing Co., Easton, Pa., 1985.

Mucosal compositions may be, for example, liquid dosage forms, such as pharmaceutically acceptable emulsions, solutions, suspensions, syrups, and elixirs. Excipients suitable for such vaccine preparations include, for example, inert diluents commonly used in the art, such as, water, saline, dextrose, glycerol, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol. Excipients also can comprise various wetting, emulsifying, suspending, flavoring (e.g., sweetening), and/or perfuming agents.

The compositions may be formulated for intranasal administration with a pharmaceutically acceptable carrier such as water, buffered saline, ethanol, polyol (for example, glycerol, propylene glycol, liquid polyethylene glycol and the like) suitable mixtures thereof, or vegetable oils. If necessary, the action of contaminating microorganisms may be prevented by various antibacterial agents, such as parabens, chlorobutanol, phenol, sorbic acid, thimerosal, and the like. It will often be preferable to include in the formulation isotonic agents, for example, glucose or sodium chloride. Such formulation may be administered intranasally as an aerosol or atomized spray, or as liquid drops.

Oral mucosal compositions also may, for example, be tableted or encapsulated for convenient administration. Such capsules or tablets can contain a controlled-release formulation. In the case of capsules, tablets, and pills, the dosage forms also can comprise buffering agents, such as sodium citrate, or magnesium or calcium carbonate or bicarbonate. Tablets and pills additionally can be prepared with enteric coatings.

"Parenteral administration" includes subcutaneous injections, submucosal injections, intravenous injections, intramuscular injections, intrasternal injections, and infusion. Injectable preparations (e.g., sterile injectable aqueous or oleaginous suspensions) can be formulated according to the known art using suitable excipients, such as vehicles, solvents, dispersing, wetting agents, emulsifying agents, and/or suspending agents. These typically include, for example, water, saline, dextrose, glycerol, ethanol, corn oil, cottonseed oil, peanut oil, sesame oil, benzyl alcohol, benzyl alcohol, 1,3-butanediol, Ringer's solution, isotonic sodium chloride solution, bland fixed oils (e.g., synthetic mono- or diglycerides), fatty acids (e.g., oleic acid), dimethyl acetamide, surfactants (e.g., ionic and non-ionic detergents), propylene glycol, dextran, lactose, trehalose, and/or polyethylene glycols. Excipients also may include small amounts of other auxiliary substances, such as pH buffering agents.

The compositions may include one or more adjuvants that enhance a subject's immune response (which may include an antibody response, cellular response, or both), thereby increasing the effectiveness as a vaccine. The adjuvant (s) may be a substance that has a direct (e.g., cytokine or Bacille Calmette-Guerin (BCG)) or indirect effect (liposomes) on cells of the subject's immune system. Examples of often suitable adjuvants include oils (e.g., mineral oils), metallic salts (e.g., aluminum hydroxide or aluminum phosphate), bacterial components (e.g., bacterial liposaccharides, Freund's adjuvants, and/or MDP), plant components (e.g., Quil A), cytokines and/or one or more substances that have a carrier effect (e.g., bentonite, latex particles, liposomes, and/or Quil A). Adjuvants also include, for example, CARBIGEN adjuvant and carbopol. It should be recognized that this disclosure encompasses both compositions that include an adjuvant (s), as well as compositions that do not include any adjuvant.

"Cytokines" used in the compositions and methods described herein, refer to small proteins secreted primarily, but not exclusively, by cells of the immune system that promote the proliferation and/or differentiative functions of other cells. Examples of cytokines include interleukins, interferons, hematopoietic colony stimulating factors (CSF), and proinflammatory factors such as tumor necrosis factor (TNF). It is contemplated that the compositions may be freeze-dried (or otherwise reduced in liquid volume) for storage, and then reconstituted in a liquid before or at the time of administration. Such reconstitution may be achieved using, for example, vaccine-grade water.

Administration of the Compositions

In accordance with particular embodiments, the composition comprising fungi having a dysfunctional CPS1 gene product is used in a vaccine preparation. In general, the vaccine is administered in an immunologically effective amount, which is an amount sufficient to induce a protective immune response in the subject against fungal infection (e.g. *Coccidioides* spp.). The live attenuated fungi described herein are capable of triggering an immune response that protects a mammal against fungal infection or colonization after one or more administrations as a live vaccine. A "protective immune response" refers to any immunological response, either antibody or cell-mediated immunity, or both, occurring in the subject that either prevents or detectably reduces subsequent infection, or eliminates or detectably reduces the severity, or detectably slows the rate of progression, of one or more clinical symptoms or conditions associated with fungal infection.

The immunogenicity level may be determined experimentally by challenge dose titration study techniques generally known in the art. Such techniques typically include vaccinating a number of subjects with the vaccine at different dosages, and then challenging the subjects with the virulent fungi to determine the minimum protective dose.

Factors affecting the preferred dosage regimen may include, for example, the age, weight, sex, diet, activity, and condition of the subject; the route of administration; the efficacy, safety, and duration-of-immunity profiles of the particular vaccine used; whether a delivery system is used; and whether the vaccine is administered as part of a drug and/or vaccine combination. Thus, the dosage actually employed can vary. Determining such dosage adjustments is generally within the skill of those in the art using conventional means.

In one embodiment, the composition is administered at a dose of at least about 500 spores of the composition, at least about 1,000 spores of the composition, at least about 10,000 spores of the composition, at least about 20,000 spores of the composition, at least about 30,000 spores of the composition, at least about 40,000 spores of the composition, at least about 50,000 spores of the composition, at least about 60,000 spores of the composition, at least about 70,000 spores of the composition, at least about 80,000 spores of the composition, at least about 90,000 spores of the composition, at least about 100,000 spores of the composition, at least about 150,000 spores of the composition, and at least about 200,000 spores of the composition.

It is contemplated that the compositions may be administered to a subject at a single time; or, alternatively, two or more times over days, weeks, months, or years. In some embodiments, the composition is administered at least two times. In some such embodiments, for example, the compositions are administered twice, with the second dose (e.g., the booster) being administered approximately one week after the first dose, approximately two weeks after the first dose, approximately three weeks after the first dose, approximately four weeks after the first dose, approximately five weeks after the first dose, approximately six weeks after the first dose, approximately seven weeks after the first dose, and approximately eight weeks after the first dose. In the above embodiments, the first and subsequent dosages may vary, such as, for example, in amount and/or form. Often, however, the dosages are the same as to amount and form.

In certain embodiments, the compositions are administered to a subject that is immunogenically naive to the fungi, e.g., the subject has not been vaccinated for the fungus or exposed to the fungus. In accordance with this embodiment, the composition is administered before the subject recipient is infected with the fungus. In such embodiments, the vaccine preparation may, for example, be administered to prevent, reduce the risk of, or delay the onset of *Coccidioides* spp. infection or one or more (typically two or more) *Coccidioides* spp. symptoms.

In some embodiments, the compositions are administered to subjects in a population after a subject in the population has been infected with the fungus. In such embodiments, the compositions may, for example, ameliorate, suppress, or eradicate the fungus or one or more (typically two or more) fungal symptoms in the subjects of the population.

The compositions can be administered by conventional means, including, for example, mucosal administration, (such as intranasal, oral, intratracheal, and ocular), and parenteral administration (such as, without limitation, intraperitoneal, subcutaneous or intramuscular administration). The compositions may also be administered intradermally or transdermally (including, without limitation, via a skin patch or topical administration). Mucosal administration is often particularly advantageous for live attenuated vaccines.

Cyclic Peptide Synthase Cps1 (CPS1)

CPS1 gene was originally identified as a potential non-ribosomal peptide synthase component, because it encodes an 1879 amino acid polypeptide with two AMP binding domains related to the adenylation domains in bacterial non-ribosomal peptide synthases. However it also contains a putative N-terminal DMAP1b domain. In mammals, this domain binds the DMAP1 transcriptional co-repressor that has been shown to bind regulatory proteins and is proposed to act as a co-repressor of transcription.

The present CPS1 deletion strains are non-pathogenic but do initiate the formation of spherules (the infectious form of *Coccidioides*). The mutants also form spherules in vitro. The CPS1 mutant appears to have great potential as an attenuated vaccine since it protects from infection. When susceptible mice are challenged with wild type *C. posadasii* after inoculation with the Δcps1 mutant strain, nearly all experience extended survival of at least four weeks and have low fungal burdens. Innoculation with the CPS1 deletion mutant results in animals that are completely resistant to infection. Other fungi can be genetically engineered to make a fungal strain having a dysfunctional CPS1 gene to make vaccines useful to treat a number of different fungal infections.

In some embodiments, the dysfunctional CPS1 gene is a result of a deletion of at least a portion of the CPS1 gene. In certain embodiments, the dysfunctional CPS1 gene product is a result of a deletion of at least about the entire CPS1 gene, at least about the entire DMAP region of the CPS1 gene, at least about an entire AMP binding domain region of the CPS1 gene, a regulatory element of the CPS1 gene, at least the coding sequence of the CPS1 gene, at least about 90% of the CPS1 gene, at least about 80% of the CPS1 gene, at least about 70% of the CPS1 gene, at least about 60% of the CPS1 gene, at least about 50% of the CPS1 gene, at least about 40% of the CPS1 gene, at least about 30% of the CPS1 gene, at least about 20% of the CPS1 gene, and at least about 10% of the CPS1 gene. In another embodiment, the dysfunctional CPS1 gene product is a result of deletion of the entire CPS1 gene.

Coccidioidomycosis (Valley Fever)

Coccidioidomycosis is a fungal infection (Valley Fever) caused by the endemic fungal species, *Coccidioides immitis* and *Coccidioides posadasii*. The disease can range from an asymptomatic infection that renders humans immune for life to a fatal respiratory or disseminated infection. Approximately 40% of 150,000 people infected annually become sick, and approximately 5% develop severe and life-threatening illness that may leave them disabled, under continuous treatment, or deceased. Among patients that develop disseminated disease, most are treated for months to years, and many who discontinue treatment suffer relapse at some point because the current drugs available suppress but do not eradicate the fungus from the body. Treatment with antifungal medication may cost between $5000-$20,000 per year, not including the costs of ancillary care such as hospitalization, rehabilitation, frequent medical care, and disability. Better vaccines and medications to treat illness, e.g., short morbidity and reduce the severity and life time sequelae of coccidioidomycosis, are desperately needed because currently available medications are primarily fungistatic and fail in a significant number of disseminated cases.

Coccidioidomycosis is commonly known as cocci or "Valley Fever", as well as "California Fever", "desert rheumatism", and "San Joaquin Valley Fever", is endemic in certain parts of Arizona, California, Nevada, New Mexico, Texas, Utah and northern Mexico.

*Coccidioides immitis* or *Coccidioides posadasii* resides in the soil in certain parts of the southwestern United States, most notably in California and Arizona. It is also prevalent in northern Mexico, and parts of Central and South America. It is dormant during long dry spells, then develops as a mold with long filaments when the rains come and that matures to break off into spores. The spores, known as arthroconidia, are swept into the air by disruption of the soil, such as during construction, farming, windstorms or an earthquake.

Infection is caused by inhalation of the particles. The disease is not transmitted from person to person. The infection ordinarily resolves leaving the patient with a specific immunity to re-infection. However, in some cases the infection may manifest itself repeatedly or permanently over the life of the host. *Coccidioides immitis* or *Coccidioides posadasii* is a dimorphic saprophytic organism that grows as a mycelium in the soil and produces a spherule form in the host organism.

Coccidioidomycosis is confined to the western hemisphere between 40° N and 40° S. Dry soil, especially in the Lower Sonoran Life Zone, is supportive of the pathogenic fungi growth. In harmony with mycelium life cycle, incidence increases with periods of dryness after a rainy season; this phenomenon, termed "grow and blow," refers to growth of the fungus in wet weather, producing spores which are spread by the wind during succeeding dry weather.

Besides humans, dogs, and cats, the fungus can be shown to infect most mammals, even if they do not get sick from it very often. Species in which Valley Fever has been found include livestock such as cattle and horses; llamas; marine mammals, including sea otter; zoo animals such as monkeys and apes, kangaroos, tigers, etc; and wildlife endemic to the geographic area such as cougar, skunk, and javelina.

In soil, *Coccidioides* spp. exists in filament form. It forms hyphae in horizontal and vertical direction. With time, cells within hyphae degenerate to form alternating barrel shaped cells, approximately 3-5 microns in size, called arthroconidia. Arthroconidia are lightweight and carried by air currents. They can easily be inhaled without the person knowing. On arriving in alveoli, they enlarge in size and internal septations are developed, forming a structure termed a spherule. Internal spores, termed endospores develop within the spherule as it matures. Rupture of the spherules release these endospores, which in turn repeat the cycle and spread the infection locally and can disseminate to any organ via the blood and lymph systems. Nodules can form in lungs surrounding these spherules. When these rupture, they release their contents into bronchus, forming thin-walled cavities. These cavities can result in symptoms like characteristic chest pain, meoptysis and persistent cough.

Aspergillosis

*Aspergillus* spp. are fungi whose spores are present in the air we breathe, but does not normally cause illness. However an individual with a weakened immune status may be susceptible to infection by some *Aspergillus* species, primarily *Aspergillus fumigatus*.

Aspergillosis is a group of diseases which can result from *Aspergillus* infection and includes invasive aspergillosis, ABPA, CPA and aspergilloma. Some asthma patients with very severe asthma may also be sensitized to fungi like *Aspergillus* (SAFS).

Aspergillosis may affect patients whose immune system may be compromised—including those with leukemia, chemotherapy patients or those on steroids, transplant patients, cystic fibrosis, HIV or AIDS, chronic obstructive pulmonary disease (COPD), chronic granulomatous disease (CGD), severe asthma with fungal sensitivity (SAFS) and many others.

*Aspergillus* does not solely affect humans; birds and animals can also develop aspergillosis, and some plant diseases and food spoilage may be due to *Aspergillus* infection. Especially serious are those *Aspergillus* species that produce the highly carcinogenic mycotoxin, aflatoxin, which can cause serious acute and chronic health problems in people who accidentally ingest it. Primarily aflatoxin producing species are *A. flavus* and *A. parasiticus*, which can contaminate foods such as maize, peanuts and cottonseeds.

Histoplasmosis

Histoplasmosis is a disease caused by the fungus *Histoplasma capsulatum*. The fungus lives in the environment, usually in association with large amounts of bird or bat droppings. Lung infection can occur after a person inhales airborne, microscopic fungal spores from the environment; however, many people who inhale the spores do not get sick. The symptoms of histoplasmosis are similar to pneumonia, and the infection can sometimes become serious if it is not treated.

Blastomycosis

Blastomycosis is a disease caused by the fungus *Blastomyces dermatitidis*. The fungus lives in moist soil and in association with decomposing organic matter such as wood and leaves. Lung infection can occur after a person inhales airborne, microscopic fungal spores from the environment; however, many people who inhale the spores do not get sick. The symptoms of blastomycosis are similar to flu symptoms, and the infection can sometimes become serious if it is not treated. *Blastomyces dermatitidis* can also infect dogs.

Candidiasis

*Candida* is a yeast and the most common cause of opportunistic mycoses worldwide. It is also a frequent colonizer of human skin and mucous membranes. *Candida* is a member of normal flora of skin, mouth, vagina, and stool. As well as being a pathogen and a colonizer, it is found in the environment, particularly on leaves, flowers, water, and soil. While most of the *Candida* spp. are mitosporic, some have known teleomorphic state and produce sexual spores.

Infections caused by *Candida* spp. are in general referred to as candidiasis. The clinical spectrum of candidiasis is extremely diverse. Almost any organ or system in the body can be affected. Candidiasis may be superficial and local or deep-seated and disseminated. Disseminated infections arise from hematogenous spread from the primarily infected locus. *Candida albicans* is the most pathogenic and most commonly encountered species among all. Its ability to adhere to host tissues, produce secretory aspartyl proteases and phospholipase enzymes, and transform from yeast to hyphal phase are the major determinants of its pathogenicity.

Cryptococcosis

*Cryptococcus neoformans* is an encapsulated yeast and the causative agent of cryptococcosis. Given the neurotropic nature of the fungus, the most common clinical form of cryptococcosis is meningoencephalitis. The course of the infection is usually subacute or chronic. Cryptococcosis may also involve the skin, lungs, prostate gland, urinary tract, eyes, myocardium, bones, and joints. The most commonly encountered predisposing factor for development of cryptococcosis is AIDS. Less commonly, organ transplant recipients or cancer patients receiving chemotherapeutics or long-term corticosteroid treatment may develop cryptococcosis.

Kits

The present disclosure further includes kits that are suitable for use in performing the methods described above. The kits can includes a dosage form of the compositions in an appropriate container and can also optionally include at least one additional component, and, typically, instructions for using the compositions with the additional component(s). The additional component(s) may, for example, be one or more additional ingredients (such as, for example, one or more of the excipients discussed above) that can be mixed with the compositions before or during administration. The additional component(s) may alternatively (or additionally) include one or more apparatuses for administering the compositions to the subject. Such an apparatus may be, for example, a syringe, inhaler, nebulizer, pipette, forceps, or any medically acceptable delivery vehicle. In some embodiments, the apparatus is suitable for subcutaneous administration of the compositions. In some embodiments, the apparatus is suitable for intranasal administration of the vaccine preparation.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims. Whenever a range is given in the specification, all intermediate ranges and sub-ranges, as well as all individual values included in the ranges given are intended to be included in the disclosure. When a Markush group or other grouping is used herein, all individual members of the group and all combinations and sub-combinations possible of the group are intended to be individually included in the disclosure.

EXAMPLES

Example 1

Material and Methods

Strains, Media and Growth Conditions

*Coccidioides posadasii* strain Silveira (ATCC 28868) was cultured on 2XGYE medium (2% glucose, 1% yeast extract and 1.5% agar) at room temperature. All manipulations of viable cultures were performed in the Keating Building Select agent biosafety level 3 (BSL3) laboratory, using standard operating procedures developed for working with this select agent and approved by the Centers for Disease Control (CDC). Δcps1 strains were selected and maintained on 2XGYE media supplemented with hygromycin at 50 μg/ml. Arthroconidia of Silveira were harvested from four-week old cultures grown on 2XGYE at room temperature using sterile water by the mini-stir bar method described previously (Huppert et al. Antimicrobial Agents and Chemotherapy, 1:367-372, 1972). Arthroconidia were washed with sterile dH$_2$O and stored in sterile dH$_2$O at 4° C. Spore counts were made with a hemacytometer counts and viable counts determined by plating. Spherules were generated by growth of strains in modified Converse medium at 37° C., 20% CO$_2$ and shaken at 180 rpm as described in J Bacteriol., 78:231-239 (1959). Spherules were harvested at 24-hour intervals up to 120 hours, fixed in 10% formaldehyde and stained with cotton blue. At least 50 spherules were measured to estimate their size at each time point. Statistical analysis was performed using SAS (version 9.1, SAS Institute Inc., Cary, N.C.) and the size of spherule is presented as mean ±SD.

Construction of CPS1 Gene Deletion Cassette

The CPS1 gene of *Coccidioides*, CIMG_03303.3, was identified via homology to the *Cochlibolus heterostrophus* CPS1 gene. A CPS1 gene deletion cassette was constructed in multiple steps using primers listed in Table 1. *C. posadasii* strain Silveira DNA was used as a template to generate PCR fragments representing the 5' and 3' flanking regions of the CPS1 gene using primers OAM 1190 and OAM 1192, and OAM 1193 and OAM 1194 respectively. Primers OAM 1192 and OAM 1193 contain sequences complementary to the ends of the hygromycin resistance gene cassette (hphB) of plasmid pCB1004. The hygromycin (hphB) gene was amplified from plasmid pCB1004 using primers OAM597 and OAM 598. The PCR products of the CPS1 5' and 3' flanking regions were mixed with that of the hphB gene and amplified with nested primers OAM 1191 and 1195, that contain EcoRI sites. The resulting PCR product was then ligated into pGEM®-T Easy (Promega, Madison, Wis.). The construct, designated pAM1567, was verified by restriction analysis and PCR and the hphB insert gene of the plasmid was sequenced to determine that no mutations had been introduced. The gene replacement construct from pAM1567, containing the CPS1 5'flank-hphB-CPS1 3'flank was cloned into the binary vector pAM1145 as an EcoRI fragment, producing plasmid pAM1594. Plasmid pAM1594 was transformed into *Agrobacterium tumefaciens* strain EHA105 by electroporation and the resulting strain was named as A1594.

TABLE 1

Primers Used

| Primer | Sense or Anti-sense | Primer sequence (5'-3') | SEQ ID |
|---|---|---|---|
| 5'UTR | | | |
| OAM1190 | Sense | GTGGGTATCAGTTGTTTGTAGGAAG | 4 |
| OAM1192 | Anti-sense | GCTCCTTCAATATCAGTTAACGTCGAGTTAA ACGCCAATCAGTATCGTCGTTTCG | 5 |
| 3' UTR | Sense | | |
| OAM1193 | Anti-sense | AGATGCCGACCGGGAACCAGTTAACATAGA CATGAGGATTGCTCGGCTTTGTC | 6 |
| OAM1194 | | TCACGATGTCGTACGGGCCAGTTTG | 7 |
| Nested | | | |
| OAM1191 | Sense | GGGAATTC<u>GAATTC</u>GCGTGGTCTGGTAGTCG CGTTGAGAGCC | 8 |
| OAM1195 | Anti-sense | GAGCCG<u>GAATTC</u>CCTAAATGCATAGCCATTC CACAAATAC | 9 |
| CPS1 Intern | | | |
| OAM1288 | Sense | CAACCGCAGGTCAGTGTATG | 10 |

Targeted Disruption of the *C. posadasii* CPS1 Gene in Strain Silveira

*C. posadasii* strain Silveira was transformed using *A. tumefaciens* strain A1594 as described previously in Eukaryotic Cell 4:111-120 (2005). Briefly, 1×10$^7$ arthroconidial germlings and 1×10$^9$ *A. tumefaciens* cells were mixed and dispersed onto six sterile 0.45 μM, 82 mm diameter nitrocellulose filters (Millipore Corporation, Bedford, Mass., USA) on plates containing AB induction media. Following co-cultivation at room temperature for 48 hours, the nitrocellulose filters were transferred onto selection plates containing 2XGYE media supplemented with 50 μg/ml hygromycin (selection for transformed strains) and 100 μg/ml kanamycin (counter selection to prevent further growth of *A. tumefaciens*). Transformants were isolated after incubation at room temperature for 1-2 weeks and grown on selection plates for sporulation. Monoconidial isolates were selected via two conidial passages as described in Eukaryotic Cell 4:111-120 (2005).

DNA Isolation and Confirmation of Transformants

Genomic DNA was isolated from putative transformants as described previously in Eukaryotic Cell 4:111-120 (2005). Briefly, mycelium from a young colony was scraped from plates and mechanically disrupted with acid-treated glass beads in lysis buffer (50 mM Tris-HCl, [pH7.5], 100 mM EDTA [pH8.0], 100 mM NaCl, 0.5% SDS and 100 mM DTT) by vortexing at 3000 rpm for 10 minutes. DNA was then purified by extraction with phenol:chloroform:isoamyl alcohol. Following precipitation, the DNA was treated with RNase A and then extracted using CTAB. The DNA was precipitated, resuspended in 50 µl sterile $dH_2O$ and stored at −20° C.

Transformed *C. posadasii* strains were analyzed by Southern blot analysis to verify replacement of the CPS1 gene by the hphB gene using standard procedures as described previously in Eukaryotic Cell 4:111-120 (2005). Probes for hybridization included the hphB gene, generated by PCR amplification from plasmid pCB1004 using primers OAM597 and OAM598, an internal fragment of CPS1 generated by amplification from Silveria genomic DNA using primers OAM1288 and OAM1289 and a 5' flanking fragment (Table 1).

Measurement of in Vitro Growth and Spherulation

To determine whether the Δcps1 strains were altered in hyphal growth and conidiation, colonial radial growth was compared to strain Silveira. Three day-old monoconidial cultures were placed on 2XGYE petri plates containing or lacking 50 µg/ml hygromycin. Strains were plated in triplicate and the growth rate was assessed at room temperature (24° C.) and at 37° C. Colony diameters were recorded at three-day intervals for 21 days. Statistical analysis was performed using SAS (version 9.1, SAS Institute Inc., Cary, N.C.) and the data is presented as mean ±SD.

Mice 8-week-old female C57/BL6 mice, were purchased from Harlan-Sprague-Dawley (Indianapolis, Ind.) and maintained according to National Institutes of Health guidelines. All studies were conducted with the approval of the Institutional Animal Care and Use Committee at the University of Arizona.

Example 2

In Vivo Studies

Pathogenicity of the Δcps1 strain was assessed in two independent mouse studies in the Animal BSL3 facility at the Department of Veterinary Sciences and Microbiology at the University of Arizona. Mice were infected intranasally following i.p. anesthetization with ketamine-xylazine as described previously in Infection and Immunity 70:3287-3289 (2002). Twelve mice were inoculated per treatment with two mice sacrificed at 14 days for histopathology and the other 10 maintained for 28 days or until they appeared moribund. Mice were treated with the following spore doses (design/actual): Silveira, 50/59 arthroconidia/mouse, Δcps1, 50/50, 250/211, 1000/810 spores/mouse. In the second study, a higher dose was used to further assess avirulence. Strain Silveira was inoculated at 50/53 arthroconidia/mouse (design/actual), while Δcps1 was infected with 4400 arthroconidia. Mice were inoculated intranasally and monitored as in the first study.

An additional mouse study was performed to test whether the Δcps1 strain could provide protection against subsequent inoculation with wild type *C. posadasii*. In this study, groups of eight mice were inoculated twice, two weeks apart, with 50,000 spores of the Δcps1 strain introduced either subcutaneously or intraperitoneally. They were then challenged intranasally four weeks after the second (booster) dose with 90 spores of wild type parental *C. posadasii*, strain Silveira. As controls, eight mice were vaccinated with a positive control chimeric antigen, $Ag2/_{PRA1-106}$ fused to CSA, and eight were vaccinated with adjuvant alone, a combination of MPL-SE (25 µg/mouse) and CpG (10 µg/mouse). The lungs of mice were weighed and quantitatively cultured two weeks after challenge.

Mice in the control group had mean lung fungal burdens of $5.3 \times 10^7$ ($800$-$11.9 \times 10^7$), while the mean fungal burden of all the mice vaccinated with CPS1 knockout was 212 cfu (range 1-1650). This avirulent strain afforded a high level of protection in a susceptible mouse, while causing no evidence of disease in 48 mice challenged with doses up 4400 spores intranasally.

Example 3

Identification of the *Coccidioides posadasii* CPS1 Gene

The CPS1 gene of *Coccidioides* spp. was identified using the *C. heterostrophus* sequence as a query (AF332878). The *C. immitis* strain RS gene CIMG_03303.3 encodes a protein of 1879 amino acids with a predicted molecular mass of 208 kDa. Alignment with the *C. heterostrophus* protein encoded by AF332878, indicated *C. immitis* CPS1 exhibited 55% identity and 13% similarity. The inventors note that the annotation for AF332878 was determined to represent a truncated form of the *C. heterostrophus* CPS1 ORF, lacking the N-terminal end of the protein which was determined based on RT-PCR (B.G. Turgeon, personal communication). Thus there is greater overall similarity between these proteins. Using BLASTX with CIMG_03303.3 against the *C. posadasii* Silveira genome identified two adjacent genes CPSG_02657.2 and CPSG_02658.2 that align consecutively with the RS CPS1 gene. Further alignment and analysis of these protein sequences with CIMG_03303.3 suggest an annotation error in Silveira; combining these proteins formed a complete open reading frame encoding the CPS1 protein. CIMG_03303.3 from *Coccidioides immitis* strain RS showed 99% identity to a *C. posadasii* strain C735 protein (*C. posadasii* strain C735 delta SOWgp, XP_003068865) and 83% identity with UREG_07134 (*Uncinocarpus reesii* 1704). The degree of similarity to *Paracoccidioides brasiliensis* ranged from 88 to 92% between the strains. The Cps1 protein is conserved in most ascomycete fungi with varying degrees of similarity to the query sequence and is related to proteins found in animals including the Dip2 proteins identified in Drosophila and found in mammals.

*C. immitis* Cps1 contains a DMAP1 binding domain at the N-terminus and two acyl-CoA synthetase (AMP-forming)/AMP-acid ligases II (CaiC) domains. The DMAP1 is known to act as a transcriptional co-repressor and the CaiC domains were found to function in lipid metabolism and secondary metabolite biosynthesis, transport and catabolism.

Example 4

Construction of a CPS1 Deletion Mutant

To understand the effect of CPS1 on virulence of *C. posadasii*, the inventors constructed Δcps1 strains using Agrobacterium mediated gene replacement. The deletion construct contained the hygromycin B gene from *Escherichia coli* between a 1.1 kb CPS1 5' flanking segment and a 1.2 kb CPS1 3'U flanking segment. The entire construct (5'flank-hph-3'flank) was cloned into pAM1145 between T-DNA border sequences at EcoRI site and transformed into *Agrobacterium tumefaciens* strain AD965 and the resulting strain designated as A1594. The *C. posadasii* Δcps1 strains were generated by co-cultivation of A1594 and *C. posadasii* germlings on induction medium, followed by the selection of transformants on plated containing hygromycin. Forty-eight hygromycin resistant transformants were picked and purified by successive re-streaking on plates containing hygromycin for three times. The CPS1 gene deletion was assessed by both PCR and Southern hybridization. DNA was extracted from 24 hygromycin resistant strains and tested for deletion cassette using primers for hph gene and the CPS1 gene in an attempt to determine if the hygromycin resistant strains were homokaryons or heretokaryons. Based on the results obtained from PCR, Southern hybridization was performed on the DNA of 17 transformants and wild type Silveira DNA restricted with EcoRI, using the hph gene, CPS1 gene, 5'flanking sequence and 3'flanking sequence amplicons as probes. When hybridized with the hph gene probe, strains 11, 19, 28 and 30, contained a 10.2 kb fragment indicative of homologous gene replacement event. All other transformants had varying sized fragments indicating ectopic integration of the deletion cassette. The transformants were further tested with wild type CPS1 gene probe and the putative gene replacement strains (11, 19, 28 and 30) lacked the wild type gene. Those which had a wild-type copy of the CPS1 gene had a fragment of 5.1 kb, including the wild-type, Silveira.

To confirm the above result the inventors tested six transformants (namely 6, 11, 13, 19, 30 and 48) and wild type with 5'flanking sequences and 3' flanking sequences as probes. All the homokaryotic transformants had a fragment of 10.2 kb with both the probes. These results support the conclusion that at least four of the transformants (11, 13, 19 and 30) tested arose from a single homologous integration event of the CPS1 deletion cassette and other strains had a non-homologous integration resulting in ectopic transformants.

Example 5

Growth Rate and Spherule Size of CPS1 Mutants

The growth rate of the Δcps1 mutant was assessed at 24° C. and 37° C. on media containing with and without hygromycin as selectable marker. Except for minor differences, no major defects in growth rates were observed between the Δcps1 and wild type during the initial growth phase. At day 5, a slightly significant difference was observed between the Δcps1 cultures grown on media containing with or without hygromycin ($p=0.0474$). However, by day 14, significant differences in growth rates between the Δcps1 and wild-type were observed in cultures grown at 24° C., where the Δcps1 had a reduced growth when compared to the wild-type. This reduced growth in the mutant might be due to the accumulation of secreted metabolites in the media. In contrast, the growth rate was almost similar between the Δcps1 and wild-type at 37° C. and correlated with the lower accumulation of the putative metabolite.

To understand the effect of the CPS1 deletion on spherule size, the inventors inoculated induction media with arthroconidia and measured the size of spherules at 24 hour intervals for a span of five days. Significant differences in spherule size were observed between the Δcps1 and wild-type at all stages of spherulation ($p<0.0001$). On day five, the maximum size of Δcps1 spherules were 7.8 μM in diameter while the wild-type spherules measured 9.9 μM.

Example 6

Comparison of Virulence of Wild-Type and Δcps1 Strains

BALB/c mice were intranasally infected with 50, 211, 810 and 4400 viable arthroconidia of Δcps1 and with 59 arthroconidia of the strain Silveira, the wild-type parental strain, to assess the virulence of Δcps1 mutants (FIG. 1). Each concentration was tested in 12 different mice and the mice were followed for 30 days post-infection. Mice challenged with arthroconidia derived from wild-type strain showed high rates of mortality and nearly 30% of the animals died by day 15; all animals were dead by 19 days post-challenge. Interestingly, all animals infected with arthroconidia from Δcps1 mutant survived the length of the study (30 days). The number of Δcps1 arthroconidia used for intranasal infections has no effect on the survival and the differences in the survival rate of mice between the wild-type and Δcps1 were significant.

The fungal burden in the mice infected with Δcps1 arthroconidia was assessed by harvesting lungs and spleens at 30 days post-challenge. From the 44 mice infected with the Δcps1 strain, only a single colony was recovered from the homogenate of the lung of one mouse infected with the 810 dose. No CFU were recovered from the spleens of the mice. Testing of the single colony recovered from the 810-dose mouse determined that it was a Δcps1 strain by PCR analysis.

Example 7

Δcps1 Strains Provide Protection Against Infection by Wild-Type *C. posadasii*

To assess whether the avirulent Δcps1 strains are able to protect mice against subsequent infection by wild type *Coccidioides*, C57BL/6 mice were vaccinated, either intraperitoneally or subcutaneously, with 50,000 Δcps1 arthroconidia, at two weeks boosted with the same number of spores and after four weeks, infected with 90 arthroconidia of Silveira, a stringent challenge as 50 spores is a lethal dose. The protective effects of the Δcps1 strain was assessed two weeks after challenge. Both lung weights and quantitative culturing of lungs revealed that the Δcps1 strain provided significant protection against infection, with a 3 log reduction in fungal burden compared to the Ag2/PRA-CSA chimeric antigen and almost a 5 log reduction compared to the adjuvant alone controls (FIG. 2).

Example 8

Sensitivity to Hydrogen Peroxide

To test whether the CPS1 deletion has any effect on resistance to oxidative stress, the inventors examined the growth of Δcps1 at different concentrations of hydrogen peroxide as a measure of oxidative stress. 2X GYE media was supplemented with different concentrations of $H_2O_2$ (0 mM to 20 mM), inoculated with either Δcps1 or wild-type strain Silveira and growth assessed at either 24° C. or 37° C. Silveira was not able to resist more than 2 mM $H_2O_2$ whereas the Δcps1 was able to grow even at 8 mM $H_2O_2$. There were significant differences between the growth of Δcps1 and wild-type at both the temperatures (24° C. and 37° C.). Hygromycin in media had an effect on oxidative stress; the Δcps1 strain was sensitive above 5 mM $H_2O_2$ when hygromycin was present in the media while in the absence of hygromycin the mutant was able to grow on media up to 8 mM $H_2O_2$ at 37° C., or 6 mM $H_2O_2$ at 24° C. These results collectively indicate that the Δcps1 mutant was able to withstand oxidative stress at a higher level compared to the wild-type strain.

Example 9

Degenerate Spherule and Endospore Formation in an Avirulent Mutant Strain of *Coccidioides posadasii* that Induces Protection in Mice.

Animals: Female BALB/c mice were purchased from Harlan-Sprague-Dawley. NOD-SCID (NSG) mice were a generous gift from Jeffrey Frelinger (Dept. Immunobiology, The University of Arizona). Animals were housed and utilized according to NIH guidelines and all procedures were approved by the University of Arizona Institutional Animal Care and Use Committee. NSG mice, which lack NK and all T- and B-cells and are severely immunodeficient, were housed under SPF (specific pathogen free) conditions until transfer into the ABSL3 laboratory for infection with *Coccidioides*.

*Coccidioides* strains: *C. posadasii* (Cp), strain Silveira, was grown to maturity on glucose yeast extract agar plates at room temperature and arthroconidia were harvested by the spin bar method. This was used as the virulent wildtype (WT) strain for challenge of vaccinated mice and as historical controls for histopathology slides to compare with Δcps1. The Δcps1 strain was transferred by plugs placed on fresh GYE plates with hygromycin in the medium and grown to maturity (8 weeks). Arthroconidia were harvested as for WT.

Mouse Studies: For lung histopathology, NSG and BALB/c mice were anesthetized with 80 mg/kg ketamine and 8 mg/kg xylazine IP and the target inoculum was instilled intranasally in 30 μl sterile saline for injection. Mice were observed and weighed to monitor clinical condition. They were sacrificed using an overdose of inhalant anesthetic and lungs fixed in 10% buffered formalin or zinc acetate fixative. Serial or step sections were cut and stained with H&E. Some studies were also stained with a *Coccidioides*-specific immunohistochemical stain.

For the protection study, 6-week old female BALB/c mice were vaccinated intranasally or subcutaneously with 10,000 viable arthroconidia of Δcps1 twice two weeks apart and challenged four weeks later with a target dose of 50 spores of strain Silveira. Control groups were vaccinated subcutaneously with MPL-SE adjuvant alone or 2 μg/mouse of chimeric antigen with adjuvant, which is known to prevent death following lethal infection in ≥90% of C57BL/6 mice. Mice were observed for 28 days and moribund animals were euthanized as necessary throughout the study. On day 28, surviving mice were sacrificed, and the lungs weighed, scored, and processed for quantitative determination of fungal burden. Colonies were enumerated after 3 days' incubation at 37° C. Spleens were plated whole on GYE plates and incubated up to one week at 37° C. to determine if disease disseminated.

Histopathology: For early studies, entire lungs of two mice per time point were cut in 5 μm sections and every fifth section was affixed to slides and stained with hematoxylin and eosin (H&E). For later studies involving higher numbers of infectious arthroconidia, two serial sections were cut for every fifth step section and 10 steps total were prepared on slides. One slide from each series was stained by H&E and one slide was immunohistochemically stained with a polyclonal goat anti-Ag2/PRA antibody that is specific for *Coccidioides* as previously described (Shubitz et al. Infection and Immunity 76:5553-5564, 2008).

Statistical Analysis: Lung fungal burdens were log transformed and compared by ANOVA (Systat 10.0).

Results

NSG mice infected with 1030 spores. Six NSG mice were infected intranasally with 1030 spores of the Δcps1 mutant strain. Mice were observed daily for lethargy, ruffled fur, inactivity, and dehydration. On day 6, two mice were sacrificed and lungs fixed in formalin. One mouse had occasional, pinpoint reddish-grey lesions scattered throughout and the other was grossly normal. Examination of step sections (every $5^{th}$ section) through the entire lungs revealed no spherules. There were clusters in the alveolar spaces of large, foamy macrophages that appeared to correlate with the grossly observable lesions, but there were no fungal forms associated with these areas. The remaining mice were observed until day 14 and all were clinically normal at sacrifice with maintenance of body weight. At necropsy, two animals had occasional reddish-grey lesions (<12) as observed in one of the mice at day 6 and the other two appeared normal. Two mice had lungs fixed in formalin and sectioned and the entire lungs of the other two were quantitatively cultured. One animal had no fungal growth and 8200 colony-forming units were recovered from the other. Again, no fungal organisms were observed in step sections through the entire lung of the two fixed mice, but the clusters of foamy macrophages in the alveolar spaces were observed. However, the recovery of 8200 colonies from one mouse suggests expansion of the infection in at least one animal because that is an 8-fold increase over the target challenge.

Figure 3A:
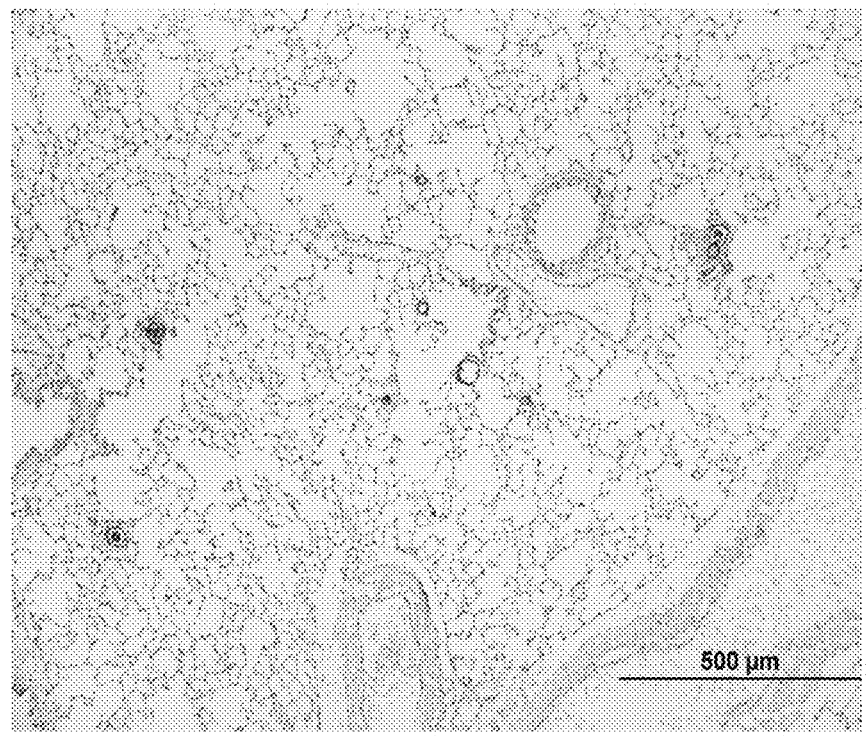
FIGS. 3A-3B. Spherule morphology comparison: NSG and C57 mice.
Figure 3B:
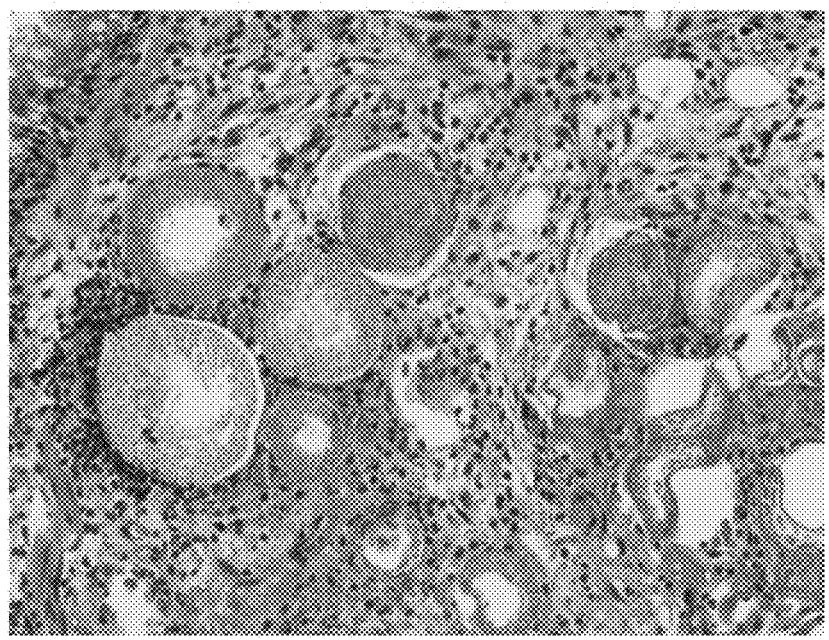
Figure 4A:
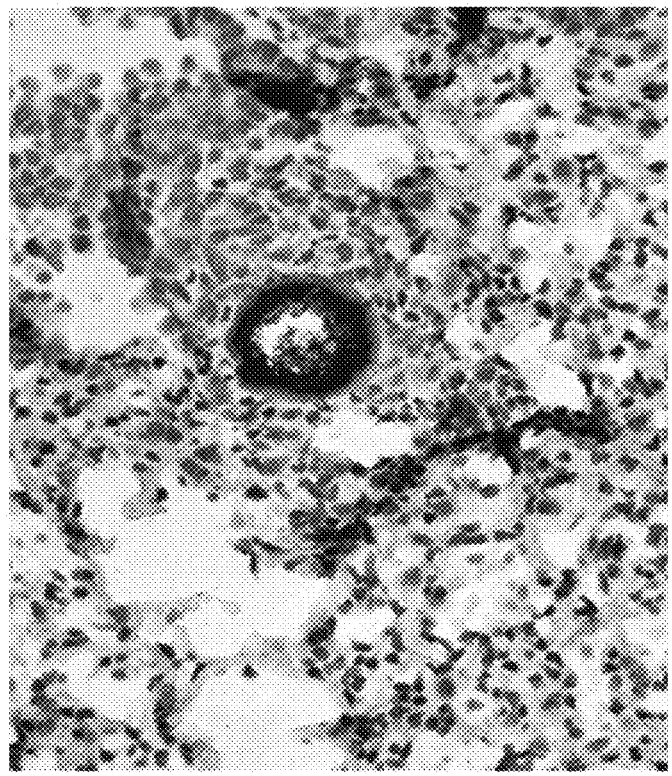
FIGS. 4A-4D. Spherule morphology comparison between WT and Δcps1 strains.
Figure 4B:
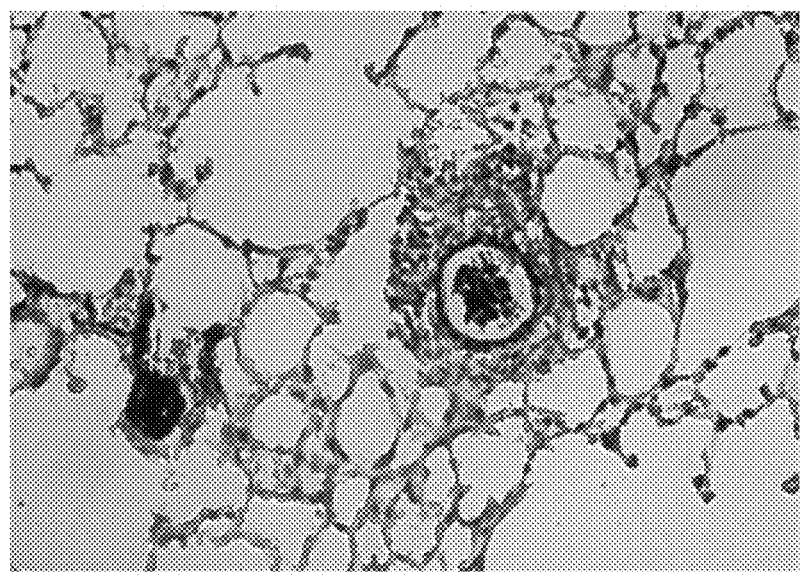
Figure 4C:
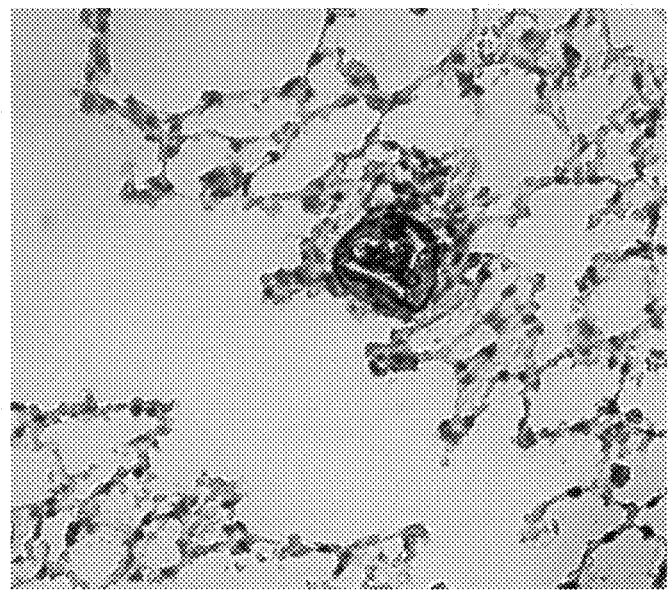
Figure 4D:
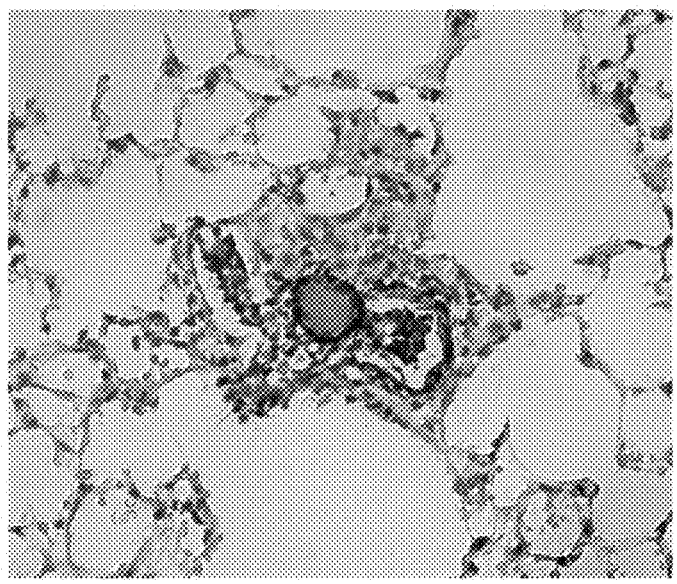
Figure 5A:
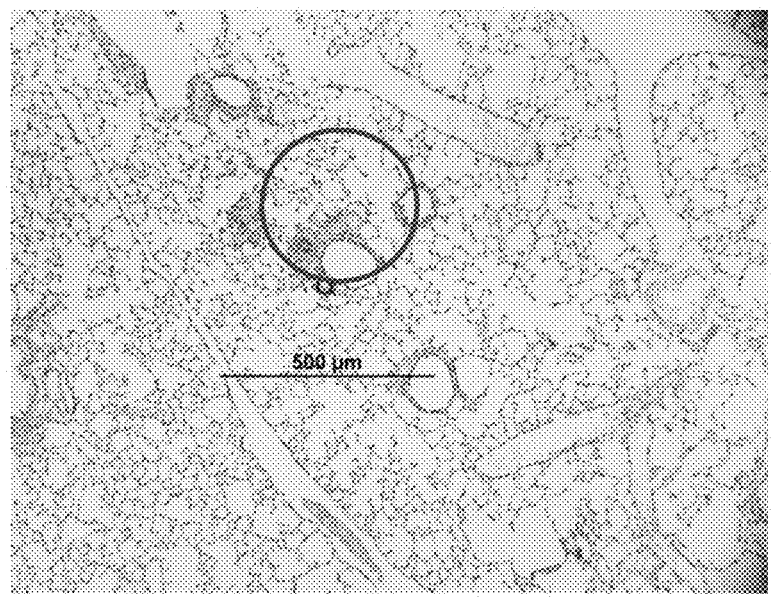
FIGS. 5A-5B. Spherule morphology comparison: BALB/c mice with Δcps1 strain.
Figure 5B:
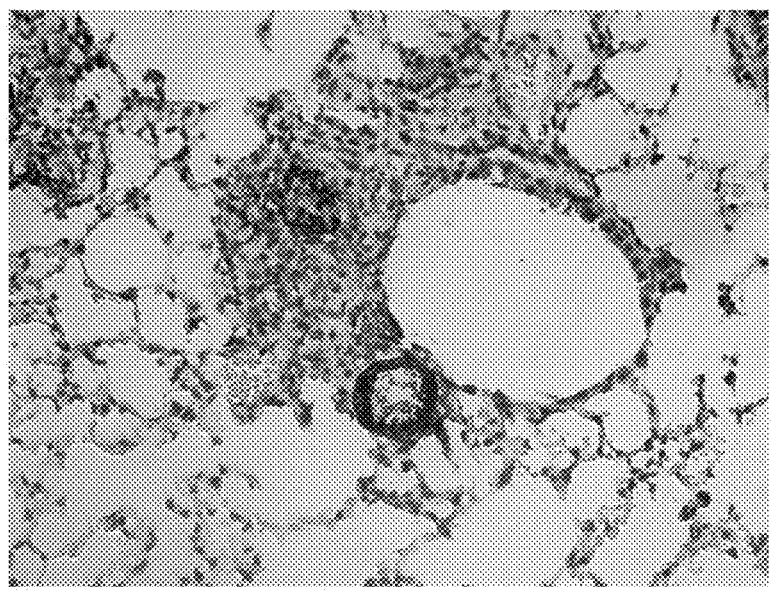
Figure 9A:
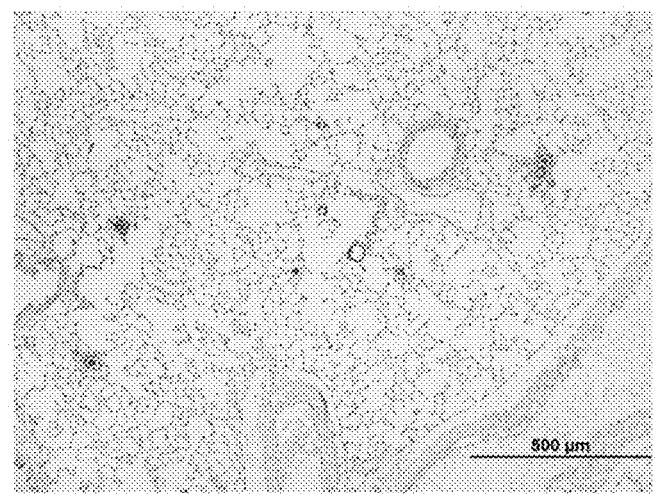
FIGS. 9A-9B. *Coccidioides*-specific staining showing variable sized spherules following Δcps1 inoculation. Two NOD-SCID and two BALB/c mice were infected intranasally with 10,000 spores of Δcps1. The sections were stained specifically for *Coccidioides* at day 3 following infection.
Figure 9B:
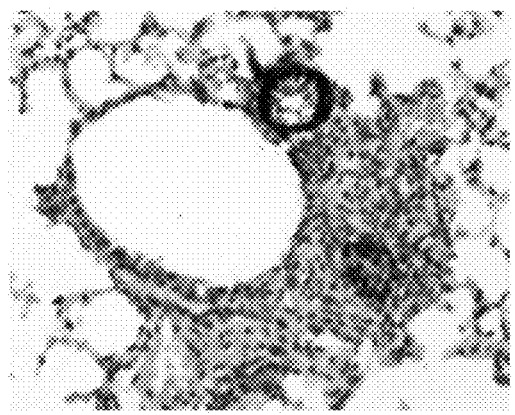
Figure 10:
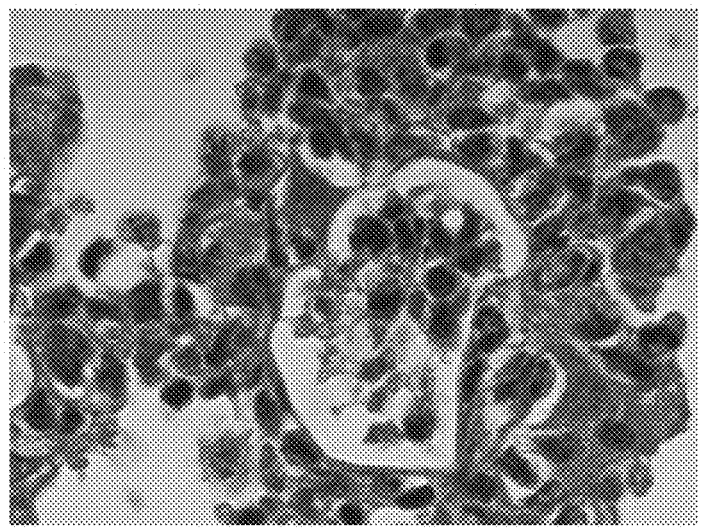
Figure 11:
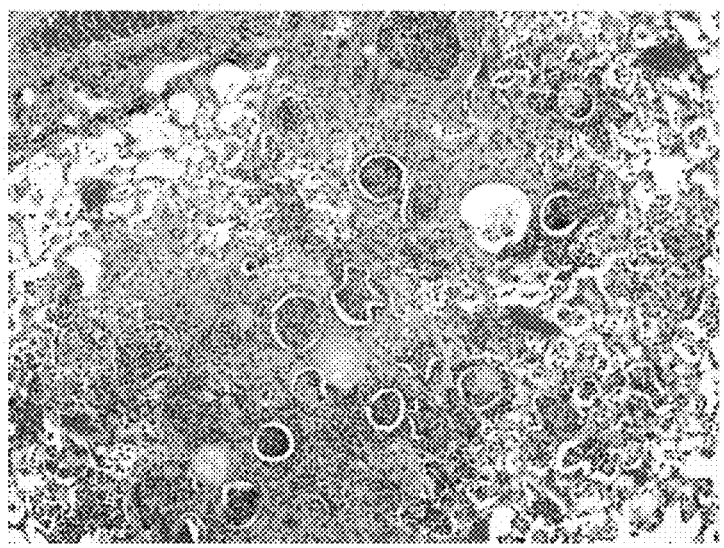
FIG. 11. H&E staining of Δcps1 spherules following rupture between day 4 and 5. Lung sections between day 4 and 5 were harvested and stained with H&E to show neutrophils around and within the degenerating spherules at low magnification. The majority of these are dead.

NSG and BALB/c mice infected with 10,000 spores. Two NOD-SCID and two BALB/c mice were infected intranasally with 10,000 spores of Δcps1 strain and one mouse of each strain was sacrificed on day 1 and day 3 post infection. Two serial sections were cut every five steps for a total of 10 steps (20 slides); one slide from each serial pair was stained with H&E and the other was stained specifically for *Coccidioides*. No organisms were seen with either stain on day 1 post infection, but the *Coccidioides*-specific stain revealed low numbers of variably sized spherules on day 3 (FIGS. 9A and 9B). There were more spherules in the NOD-SCID mice than the BALB/c mice, but the pathology in both strains was minimal. Spherules generally appeared thin walled and degenerating and were surrounded by clusters of neutrophils. This is in contrast to wildtype spherules of strain Silveira in mice at day 3, which appear to have thicker walls and are very round, often with dark-staining contents. Though abnormal spherule forms can be seen in tissue due to cutting artifact, the degenerating condition of the Δcps1 spherules appears to be constitutional. While day 3 spherules of strain Silveira appear to have one to a few layers of macrophages surrounding them, the Δcps1 spherules are surrounded, and sometimes invaded, by neutrophils. (FIG. 9A and FIG. 9B). Neutrophils do not become a significant cell type around normal spherules until rupture between day 4 and 5 (FIG. 10). It has been previously reported that spherule rupture and endospore release attracts neutrophils to the site. Whether the degenerating condition of the walls of Δcps1 spherules is a chemoattractant for neutrophils or whether the neutrophils have a role in the condition of the spherules is currently unknown; however, FIGS. 3A and 3B show that some spherules of Δcps1 appear abnormal without a neutrophilic infiltrate and it is possible that a defect in fungal wall structure may be allowing substances that normally only attract neutrophils upon rupture to escape from the Δcps1 spherules during earlier development. BALB/c mice (very susceptible, doses as low as 10 spores IN lethal) were vaccinated IN and subcutaneously (SC) with Δcps1 strain, challenged with 50 spores WT *Coccidioides*. First the mice were infected with 1030 spores, sacrificed on days 6 and 14 post-infection for histopathology. Histopathology from about 150 serial sections that were stained with H&E (routine stain) were negative for organisms. None of the mice became ill or died. For mice infected with 10,000 spores; no mice became ill and were sacrificed on days 1 and 3. Serial sections were stained with a *Coccidioides*-specific stain. Spherules were visualized at Day 3 using the *Coccidioides*-specific stain in both strains of mice; more spherules were present in the in NSG mice; the spherules look degenerate (FIGS. 3A and 3B).

Upon initial scanning, spherules were not observed on the H&E stained slides due to the paucity of organisms and the degenerating walls that either take up stain poorly or do not stain at all. Because the inventors had serial sections to examine, the H&E stained slides were reviewed again after locating spherules with the *Coccidioides*-specific stain. Low power scanning of the slides revealed the sites of neutrophil accumulation and examination of several of these sites at higher power (400-1000×) revealed remnants of spherule walls, or outlines of walls with neutrophils both surrounding the original spherule and filling it in, leaving an outline where the wall existed or where fragments may still be seen at high power (FIG. 10). One small, empty, thin-walled spherule was observed intact, but clearly is not undergoing endosporulation. (FIG. 10).

BALB/c mice infected with 25 million spores. Mice were given an overwhelming dose of Δcps1 spores in order to make more observations of the spherules in vivo and to determine the fate of the spherules over time since in all previous studies (n=3) where lower doses were used, the organism was entirely cleared and there was no residual lung inflammation by day 14 post-infection. Eight BALB/c mice were given $25 \times 10^6$ spores intranasally; two mice were sacrificed on day 1 post-infection, one mouse each on day 3 and day 4, two mice on day 5, one mouse on day 7 and one mouse on day 10. Clinically, the mice began to look lethargic and have ruffled fur on day 3 and two mice, instead of one, were sacrificed on day 5 because they appeared ill enough that maintaining them longer would constitute unnecessary suffering. The remaining two mice improved clinically after day 5 and appeared outwardly normal at the time of sacrifice.

All mice had grossly visible lesions in the lung except for the mice sacrificed at 24 hours. The lesions of mice on days 3-5 were diffuse, large, and pale and appeared edematous or "wet" rather than having discrete 0.5-1.0 mm granulomas typical of early coccidioidal infection in mice. The mice sacrificed on days 7 and 10 had grossly normal lungs. Five pairs of serial sections were made for each mouse and one of each pair was stained with H&E and the other with the *Coccidioides*-specific stain. H&E stains revealed that the mice developed a severe suppurative pneumonia with edema by day 3. The beginnings of this are apparent on day 1, but it is diffuse by day 3. The neutrophil is the primary inflammatory cell present. In addition, there are vast numbers of developing Δcps1 spherules in clusters in the middle of the suppurative response. As with the sporadically visualized spherules from the mice infected with 10,000 spores, they are highly variable in size and many are degenerating, but some appear to be attempting to endosporulate.

On day 4, the largest proportion of the Δcps1 spherules have been invaded by neutrophils, but structures that appear to be endospores are readily visible within spherules. They are highly variable in size and have thin walls like the Δcps1 spherules themselves. WT spherules rupture between day 4 and 5.

On day 5 the Δcps1 spherules appear similar to day 4, however, they are distinct from WT in that the endospores have not been released or spread out from the spherule as happens with normally rupturing spherules. (FIG. 10). All of the endospores, even those where the walls of the parent spherule are degenerated, are completely surrounded by neutrophils which appear to be containing them in their original position. In terms of the general inflammatory response, by day 5 a granulomatous component is seen. Macrophages have moved into peripheral positions surrounding the neutrophils and early granuloma formation is present. With wildtype spherules, the macrophages are present prior to the arrival of the neutrophils in the early lesion.

By day 7 post-infection, the Δcps1 spherules appear to be decreased by ≥90% compared to day 5 (visual estimate) and the inflammation is characterized by granulomas with a core of neutrophils and spherules.

Figure 12:
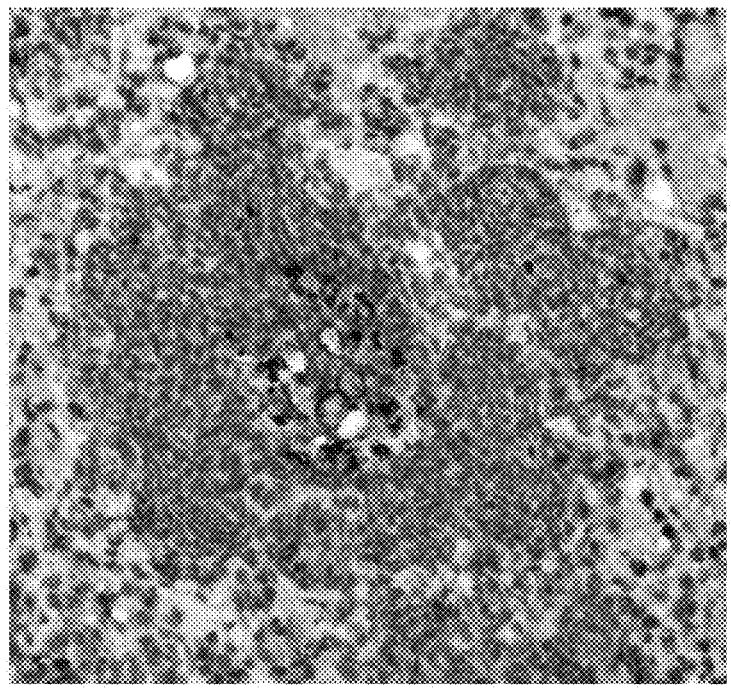
FIG. 12. Δcps1 spherule day 5 post-infection. The endospores are heavily surrounded by host neutrophils and are not dispersing or enlarging to make new spherules. *Coccidioides*-specific stain, 40× magnification.
Figure 13A:
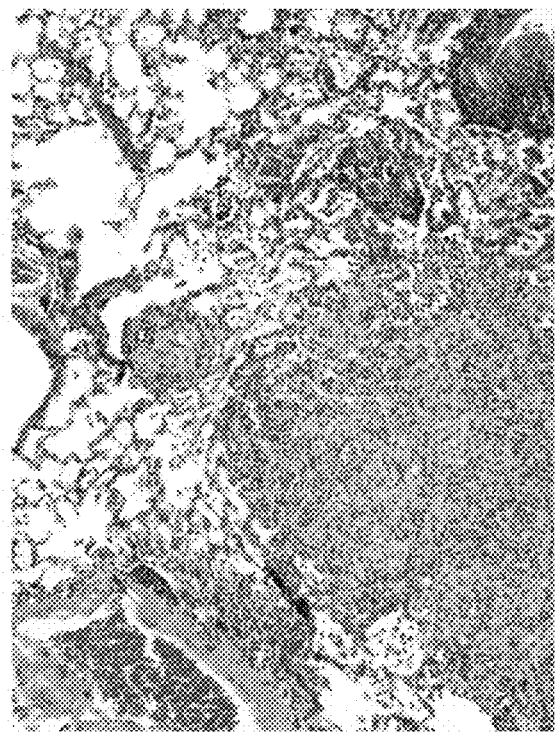
FIGS. 13A-13B. Spherules at 10 days following infection with Δcps1. 10 days following infection lung sections were taken and stained to show scattered granulomas with fewer than a dozen empty spherules within.
Figure 13B:
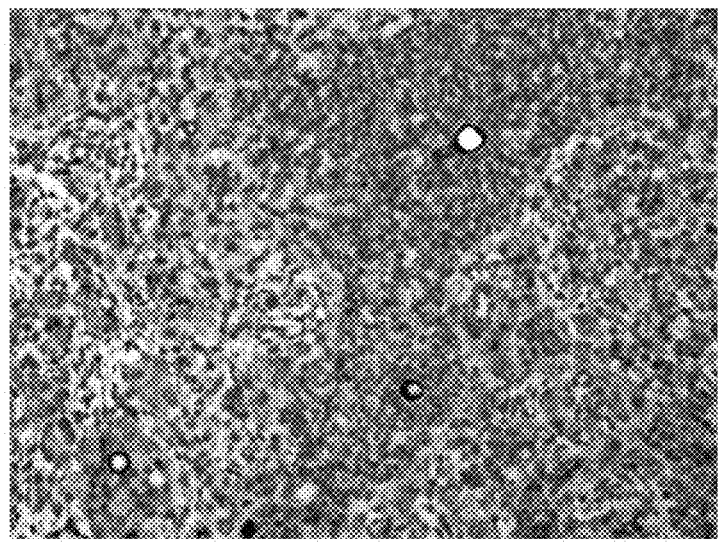

By day 10, the infection is reduced to small, scattered granulomas with fewer than a dozen primarily empty spherules within (FIG. 12).

Protection of BALB/c mice by intranasal or subcutaneous vaccination with viable Δcps1. The inventors have previously demonstrated that C57BL/6 mice can be significantly protected against lethal *Coccidioides* infection by immunizing with live spores of Δcps1. Because the inventors have been able to show good protection of C57BL/6 mice but poorer protection of BALB/c mice with recombinant vaccines in the past, and because in these experiments BALB/c mice are more susceptible to infection than C57BL/6 mice, the inventors compared BALB/c mice vaccinated with Δcps1 versus the Ag2/PRA-CSA chimeric recombinant vaccine that protects approximately 90% of C57BL/6 mice against challenges of 50 spores.

Figure 6:
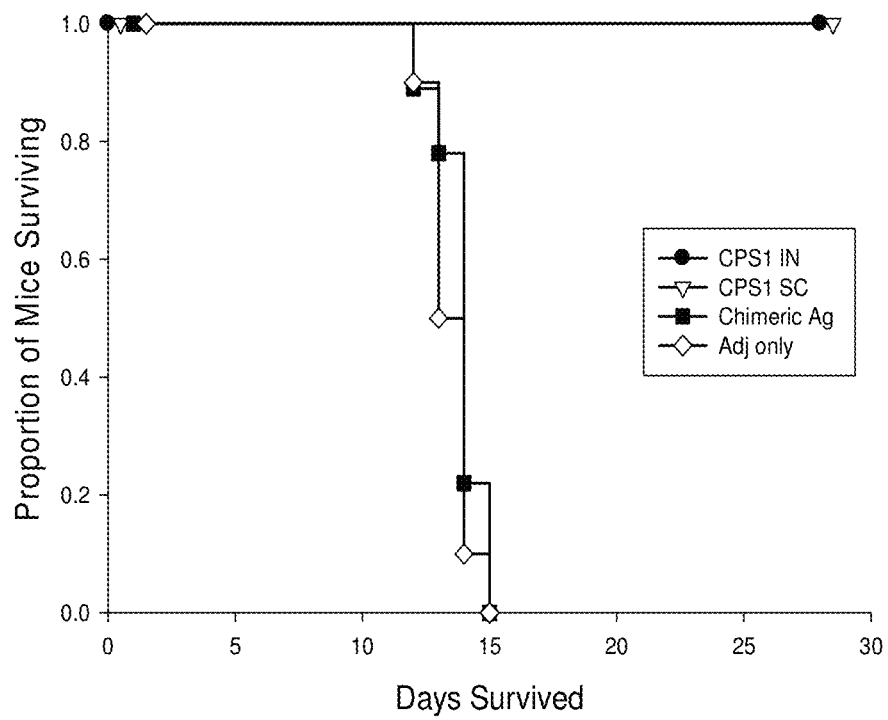
FIG. 6. Effects of vaccination of BALB/c mice with attenuated Δcps1 strain on wild type infection. Proportion of mice surviving following injection with wild type Silveira strain following vaccination with Δcps1 strains intranasally (circles), Δcps1 strain injected subcutaneously (triangle), positive control chimeric Ag (squares) or adjuvant alone (diamonds).
Figure 7:
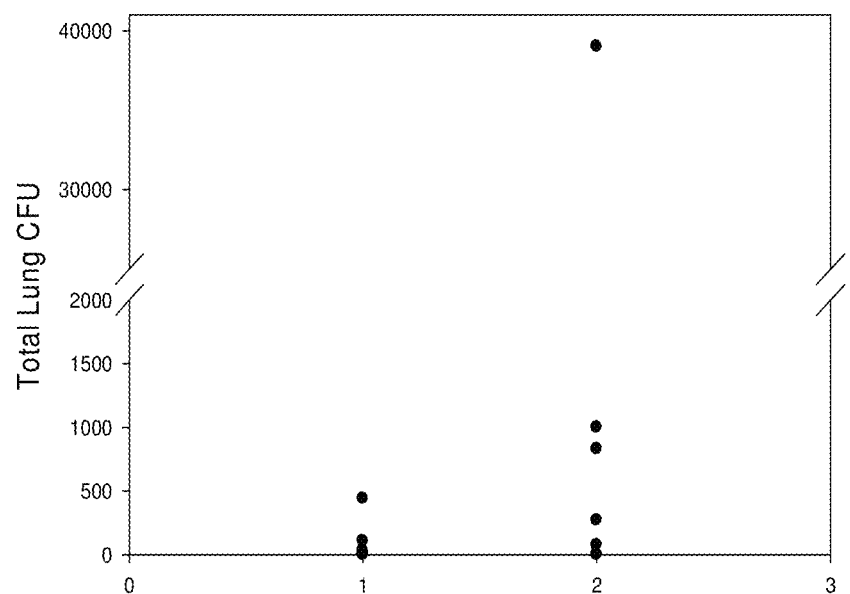
FIG. 7. Lung fungal burden of vaccinated BALB/c mice surviving 28 days after infection. Total lung colony forming units (CFU) was measured in surviving mice 28 days after infection with 46 spores of the wild type strain Silveira. Group 1 represents those that received intranasal vaccination with Δcps1 strain. Group 2 represents those that received subcutaneous vaccination with Δcps1 strain.
Figure 8:
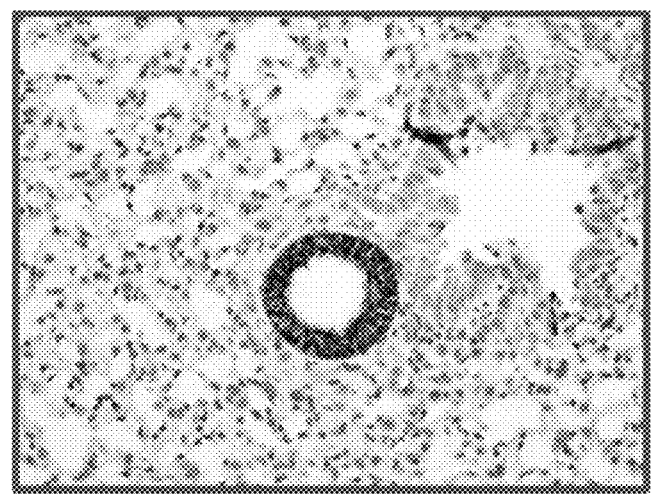
FIG. 8. *Coccidioides*-specific staining showing wild type strain spherule formation. Characterized by thick walls with well-developed endospores at day 4; very little host inflammatory reaction surrounding it. Swiss-Webster mouse, high magnification.

BALB/c mice vaccinated with the recombinant antigen or adjuvant only all died between days 13-15 post-infection, whereas all but one of the mice vaccinated with Δcps1 survived until day 28 (P<0.001) (FIG. 6). There was no statistical difference between the route of vaccination with the Δcps1. Lung fungal burdens were quantified for surviving mice on day 28 and even though the intranasally vaccinated mice had lower fungal burdens (FIG. 7), there was no statistical difference between the groups (P=0.241).

Example 10

Virulence of Mutant Strains Compared to Wild Type Silveira in Susceptible Mice.

8 week old C57BL/6 female mice were infected with target doses as listed in Table 2 with spores counted in the lungs.

TABLE 2

Type and Amount of Spores Inoculated and Present in Lungs.

| Group | Fungus | Spores inoculated | Number of mice | Spores counted in lungs |
|---|---|---|---|---|
| 1 | WT | 50 | 12 | 59 |
| 2 | Δcps1 | 50 | 12 | 51 |
| 3 | Δcps1 | 250 | 12 | 211 |
| 4 | Δcps1 | 1000 | 12 | 810 |
| 5 | ΔLOM | 50 | 12 | 51 |
| 6 | ΔLOM | 250 | 12 | 310 |
| 7 | ΔLOM | 1000 | 12 | 900 |

Mice in the L-ornithine monooxygenase mutant (ΔLOM) 1000 spore and 250 spore groups started to become moribund on day 9 and day 10, respectively. All of the 1000 spore mice were euthanized on day 9 and the 250 spore mice were euthanized on days 10 and 11. Disease scores were high in all animals, except a single mouse (#10) in ΔLOM 1000 group. The animal lungs were positive for growth, but likely this mouse received only a fraction of the target dose. Wild type mice (59 spores) became moribund on days 13-19, and the ΔLOM 50 mice on days 13-16. These two groups appeared clinically similar and had similar disease scores at necropsy.

The Δcps1 infected mice remained healthy throughout the observation period of 4 weeks. Though the original plan was to quantitate the fungal burden at the end of the study with any remaining mice, a modified plan was made to plate entire lungs and spleens if animals had no gross evidence of disease at necropsy. None of the mice had observable lesions at day 28 post-infection, and none of the slides from day 11 post-infection showed any pockets of spherules or any inflammation, not even perivascular/peribronchial infiltrates. Tissues were incubated on GYE agar plates for 9 days.

One mouse (#9, 1000 Δcps1 spore group) had growth in the lung but not the spleen. The strain that grew from this lung was saved for analysis. Statistical analysis of the survival curves was performed using a Kruskal-Wallis. 1) ΔLOM at each dose was statistically different from the other doses ($p<0.001$). 2) ΔLOM 50 sp was significantly different from WT 59 spores ($p<0.001$), with the mutant mice having earlier deaths than the WT mice. This occurred with a Δste12 *C. posadasii* mutant as well. Histologically, no differences were seen between the WT mice and ΔLOM mice on HE stained slides. 3) ΔLOM at the higher doses was also significantly different from WT 59 sp. 4) None of the Δcps1 groups was different from each other ($p=1.0$), and all were different from the other strains.

Histopathology: The ΔLOM mice did not appear different from the WT mice when inoculated with a similar dose (~50 spores). The ΔLOM mice inoculated with higher doses had enormous numbers of spherules/endospores in all fields of the lungs. Δcps1 infected mice had no evidence of infection or inflammation in the lung sections examined. Though entire lungs were submitted in 10% formalin, only a single slide with a single slice of tissue was reviewed.

Fungal burden: Nothing was quantitated in this study because of the moribund condition of 4 groups prior to the scheduled date of sacrifice and the lack of gross lesions in the remaining 3 groups of mice. For moribund mice, disease scores were 3-4 L with 6 mice also having visible lesions on the spleen. Growth was present in both lungs and spleen of most mice (with the exception of 2 ΔLOM 1000 mice which had no growth in spleen). For the healthy-appearing Δcps1 infected mice, plating of entire lungs and spleens yielded growth from the lung of a single mouse inoculated with 810 spores. This confirms that the mutant strain can reproduce in the host, but that the virulence of the strain is greatly diminished.

Example 11

Evaluation of a RYP1 Knockout in *Coccidioides.*

The RYP1 gene (Nguyen and Sil, 2008, Proceedings of the National Academy of Sciences, USA 105:4880-4885) was knocked out in *Coccidioides* strain Silveira. Deletion of the RYP1 gene leads to avirulence in *Histoplasma capsulatum* because the mold cannot switch to the pathogenic yeast phase. In *Coccidioides*, deletion of the RYP1 gene (CIMG_02671.3) appears to inhibit the change to the spherule/endospore phase in vitro and is therefore anticipated to be entirely avirulent. This strain was compared with high doses of Δcps1.

8 week old C57BL/6 mice were challenged with Δryp1 spores, Δcps1 spores and WT spores in doses shown in Table 3, with the post infection plate count.

TABLE 3

Infection of Mice with Δryp1, Δcps1 and WT Spores.

| Type of spores | Amount of spores | Number of mice | Post infection plate count |
|---|---|---|---|
| WT | 50 | 12 | 53 |
| Δcps1 | 1000 | 12 | 4400 |
| Δryp1 | 50 | 12 | 47 |
| Δryp1 | 1000 | 12 | 994 |

Mice infected with the WT strain began to become moribund on day 12 post-infection. The largest proportion were moribund on day 14. By day 19, all WT mice were dead except one animal that demonstrated weight gain and was suspected to be uninfected. The Δcps1 and Δryp1 inoculated mice remained clinically normal. The #11 and #12 mice from each group were sacrificed for histopathology on day 14. Mice challenged with Δcps1 and both doses of Δryp1 had no weight loss and no observable lung lesions. The #11 WT mouse was also negative for lung lesions and had no weight loss, but #12 was as expected. At sacrifice at 28 days, the living WT mouse had one medium sized granuloma in the lung and two splenic granulomas. All the mutant Δcps1 and Δryp1 inoculated mice were grossly negative. Organs were plated in toto on GYE plates.

All the organs plated except from the WT mouse were negative, both spleens and lungs, after 8 days of incubation. Histopathology of organs of the Δcps1 and Δryp1 infected mice 14 days post-infection showed no organisms in any of the mice. A couple of animals had mild, focal, inflammatory lesions, only 1 per mouse. No organisms were seen. WT #11 had no histologic evidence of disease, while #12 had a score of 4/5 for lungs, plus abscesses that consist almost exclusively of neutrophils and spherules/endospores in the spleen. Average days survived and average infection and sacrifice weights are provided in Table 5.

The Δcps1 strain appears in this corroborative study to be nonpathogenic, and the Δryp1 strain was also nonpathogenic, as expected based on work done with the ortholog of this gene in *Histoplasma capsulatum* (Nguyen and Sil, 2008, Proceedings of the National Academy of Sciences, USA 105:4880-4885). The survival of two WT mice was unusual and likely due to technical issues, such as the mouse swallowing the dose instead of inhaling it. It is seldom observed that C57BL16 survive to 4 weeks if infected, but this animal did have systemic disease as evidenced by growth of Coccidioides from the spleen as well as lungs.

TABLE 5

Survival and Weights of Mice Used in Study.

| Mouse# | Avg. Day survived | Avg. Infection weights | Avg. Sacrifice Weights |
|---|---|---|---|
| Δryp1 50 | 24.9 | 19.2 | 21.3 |
| Δryp1 100 | 24.9 | 19.8 | 22.0 |
| Δcps1 5000 | 24.9 | 19.9 | 22.1 |
| WT 50 | 15.5 | 19.3 | 15.2 |

Example 13

Evaluation of Immunity Provided by Avirulent Coccidioides Mutants Following Inoculation.

A study was performed to determine if two of the avirulent Coccidioides mutants will provide immunity to mice as a vaccine. Δryp1 and Δcps1 knockouts are the most interesting of the avirulent strains studied. Ryp1 is required to form spherules/endospores as the lack of the gene prevents the fungus from undergoing the transformation. Cps1 is involved in small molecule synthesis, and the gene product is required for pathogenicity.

6 week old, female, C57BL/6 mice were inoculated with Δryp1 spores, Δcps1 spores, Chimeric Ag2/PRA-CSA antigen only (Chim Ag), HSPvar only (HSF), and Adjuvant plus Sac Supe (Sac Supe) with the amount and injection method shown in Table 6. SC=subcutaneously. IP=intraperitoneal. Average lung weights are also shown in Table 6.

TABLE 6

Effects of Δryp1 and Δcps1 Inoculation on Lung Weights.

| Group | Spores inoculated | IP/SC | Number of Mice | Avg Lung weight (g) |
|---|---|---|---|---|
| Δcps1 | 50000 | IP | 8 | 0.3 |
| Δcps1 | 50000 | SC | 8 | 0.3 |
| Δryp1 | 50000 | IP | 8 | 0.79 |
| Δryp1 | 50000 | SC | 8 | 0.8 |
| HSF 2 µg | | SC | 8 | 0.6 |
| Chim Ag 2 µg | | SC | 8 | 0.4 |
| Sac Supe 2 µg | | SC | 8 | 0.7 |

Mice receiving the mutant strains were given 5000 viable arthroconidia of the respective strain intraperitoneally or subcutaneously. All animals were boosted at 2 weeks, then rested for 4 weeks before being challenged intranasally with 50 arthroconidia of C. posadasii WT strain Silveira. Mice were sacrificed two weeks after challenge. Peritoneal lesions and subcutaneous injection sites had culture and histopathology performed at necropsy.

Mice were challenged intranasally with wild type strain Silveira 4 weeks after boosting. Post-infection plate counts revealed that the mice received 90 spores. The 90 spores is a pretty stringent challenge.

Mice had weight loss in groups 3, 4, 5, and 7 by day 10 post-infection. With fluid support, most mice survived. Two mice died. Disease scores were recorded, but this time lung weights were captured as a better form of data to subject to statistical analysis. Disease scores and lung weights correlated pretty well, but the lung weights are not subjective and don't depend on separating a continuum of disease, especially in mice that are borderline between 2 and 3 and 3 and 4 disease scores. Almost all mice injected with Δcps1 mutant strain had visible granulomas in the subcutaneous tissues or 1-2 mm white lesions in the omentum. These were collected for culture.

The injection of the Δcps1 mutant strain either IP or SC resulted in the lowest lung weights in this experiment. All animals had evidence of a granulomatous lesion at the injection site, indicating that the mutant strain may have reproduced locally, providing sufficient antigen to result in a memory response that led to protection. A few IP injected animals also had 1-2 mm granulomas in the omentum. The Δryp1 strain appeared to provide no protection to the mice. This could be because it undergoes no growth at all in the host and the 25,000 arthroconidia are not sufficient to induce a memory response in the mice.

Figure 14:
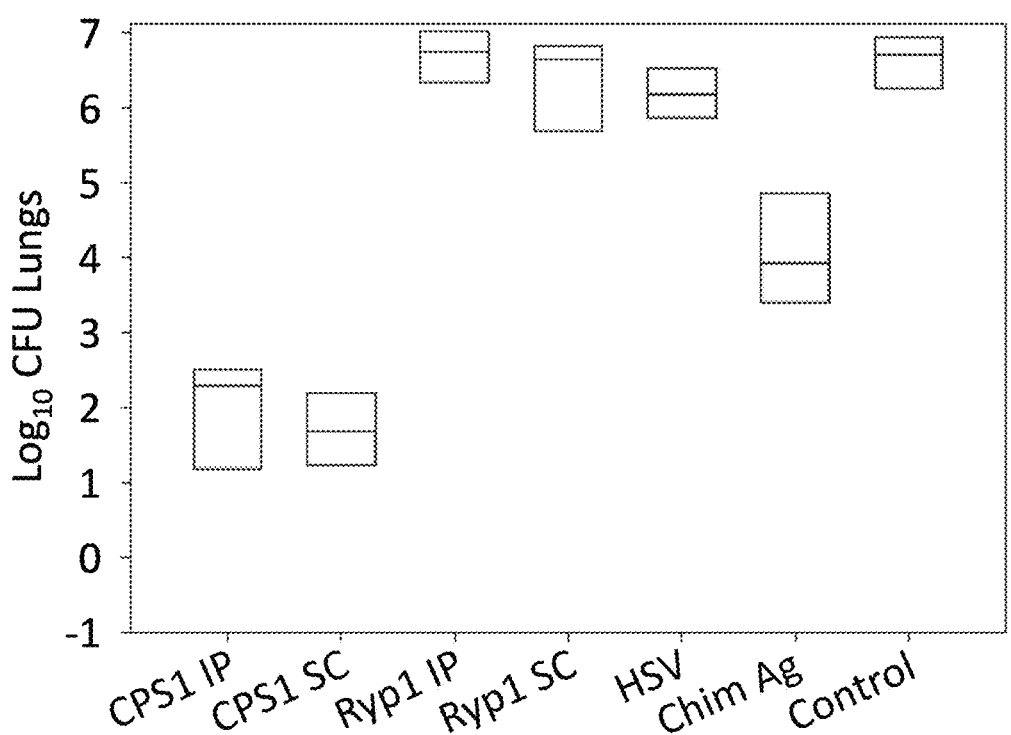
FIG. 14. Lung fungal burden following IP and SC vaccinations of Δcps1 spores, Δryp1 spores, and controls. Box plot of lung fungal burden from mice vaccinated with Δcps1 or Δryp1 spores, either IP or SC, compared to controls.

Quantitative Lung Cultures: Box plot of the CFU from the seven groups in the study. It is clear that the Δcps1 mutant offered the greatest protection with a 2 log lower average lung weight compared to the positive control chimeric antigen group (FIG. 14). None of the other vaccine groups showed protection compared to control and the statistical analysis of both lung weights and total lung CFU bear this out.

Chimeric antigen, the "gold standard" resulted in 2 logs higher lung fungal burden than the Δcps1 strain but had significant reduction (~3 logs) in fungal burden compared to controls. Mice looked pretty comparable to those in other studies with a similar challenge (~100 spores). While this is the positive control antigen in the studies, it was known that there is room for a better antigen and this study again reinforces that.

What is claimed is:

1. An immunogenic vaccine composition for use in a non-human animal for protection against coccidioidomycosis, comprising:
   a *Coccidioides arthroconidia* having a genetically modified or missing cyclic peptide synthase (CPS1) protein that renders the *Coccidioides arthroconidia* avirulent; and
   a pharmaceutically acceptable carrier.

2. The immunogenic vaccine composition of claim 1, wherein the non-human animal is selected from the group consisting of: a cat, horse, bovine, and camelid.

3. The immunogenic vaccine composition of claim 1, wherein the non-human animal is a dog.

4. The immunogenic vaccine composition of claim 1, wherein the vaccine composition is formulated for intranasal administration.

5. The immunogenic vaccine composition of claim 1, wherein the vaccine composition is formulated for subcutaneous administration.

6. The immunogenic vaccine composition of claim 1, wherein the CPS1 protein is genetically modified or missing by deletion of at least a portion of the CPS1 gene encoding the CPS1 protein.

7. The immunogenic vaccine composition of claim 1, wherein the CPS1 protein is genetically modified or missing by deletion of the DNA methyltransferase-associated protein (DMAP) binding domain region of the CPS1 gene encoding the CPS1 protein.

8. The immunogenic vaccine composition of claim 1, wherein the CPS1 protein is genetically modified or missing by deletion of the adenosine monophosphate (AMP) binding domain region of the CPS1 gene encoding the CPS1 protein.

9. The immunogenic vaccine composition of claim 1, wherein the CPS1 protein is genetically modified or missing as a result of a deletion of at least one regulatory element of the CPS1 gene encoding the CPS1 protein.

10. The immunogenic vaccine composition of claim 1, wherein the CPS1 protein is genetically modified or missing as a result of a deletion of at least 10% to at least 90% of the CPS1 gene encoding the CPS1 protein.

11. The immunogenic vaccine composition of claim 1, wherein the CPS1 protein is genetically modified or missing as a result of at least one nucleotide substitution in the CPS1 gene encoding the CPS1 protein.

12. The immunogenic vaccine composition of claim 1, wherein the CPS1 protein is genetically modified or missing as a result of at least one insertion in the CPS1 gene encoding the CPS1 protein.

13. The immunogenic vaccine composition of claim 1, wherein the CPS1 protein is genetically modified or missing as a result of at least one interruption in the CPS1 gene encoding the CPS1 protein.

14. The immunogenic vaccine composition of claim 1, wherein the *Coccidioides arthroconidia* are *Coccidioides posadasii arthroconidia* or *Coccidioides immitis arthroconidia*.

15. A method of inducing protection against coccidioidomycosis in a non-humam animal comprising administering the immunogenic vaccine composition of claim 1 to the non-human animal.

16. The method of claim 15, wherein the non-human animal is selected from the group consisting of: a cat, horse, bovine, and camelid.

17. The method of claim 15, wherein the non-human animal is a dog.

18. The method of claim 15, wherein administering the vaccine composition comprises intranasally administering the vaccine composition.

19. The method of claim 15, wherein administering the vaccine composition comprises subcutaneously administering the vaccine composition.

20. The method of claim 15, wherein administering the vaccine composition comprises administering the vaccine composition by a syringe, an inhaler or a nebulizer.

21. The method of claim 15, wherein administering the immunogenic vaccine composition comprises administering a first dose of the immunogenic composition followed by a second dose of the immunogenic composition within three weeks of the first dose.

22. The method of claim 15, wherein administering the immunogenic vaccine composition comprises administering a first dose of the immunogenic composition followed by a second dose of the immunogenic composition within two weeks of the first dose.

* * * * *

SEQUENCE LISTING

<160> NUMBER OF SEQ ID NOS: 10

<210> SEQ ID NO 1
<211> LENGTH: 1879
<212> TYPE: PRT
<213> ORGANISM: Coccidioides immitis

<400> SEQUENCE: 1

Met Ala Glu Glu Asn Pro Glu Leu Gln Ala Ala Leu Arg Glu Leu Asp
1               5                   10                  15

Gln Glu Leu Glu Asp Gly Asp Ile Thr Glu Lys Gly Tyr Gln Lys Arg
            20                  25                  30

```
Arg Thr Leu Leu Leu Ser Gln Tyr Leu Ser Ala Asp Gly Ala Gln Gly
        35                  40                  45

Asn Gln Glu Leu Arg Phe Met Arg Arg Pro Ser His Asp Ala Pro Thr
 50                  55                  60

Thr Ile Ala Gly Gly Gln Val Asn Arg Arg Ser Val Tyr Ala Asp Asn
 65                  70                  75                  80

Arg Arg Gln Ser Asp Tyr Leu Pro Ala Asn Leu Leu Ser Pro Ala Asp
                 85                  90                  95

Ser Gly Tyr Thr Asp Pro Arg Ala Asn Pro Leu Ser Arg Ile His Glu
                100                 105                 110

Asn Glu Leu Gly Phe Ser Leu Asn Pro Thr Gln Gln Pro Ser Arg Thr
            115                 120                 125

Ser Tyr Asp Ser Met Gln Ala Pro Met Ala Asn Pro Ser Val Ala Asp
            130                 135                 140

Tyr Asp His Ser Arg Ser Pro Thr Val Ile Ser Gln Asn Tyr Ala Phe
145                 150                 155                 160

Asn Pro Asn Glu Gln Pro Glu Tyr Asp Ser Leu Thr Arg Asn Ser Thr
                165                 170                 175

Met Leu Asp Ser Gln Glu Ala Tyr Phe Ser Asp Phe Ala Gly Glu Gln
            180                 185                 190

His Asp Glu Arg Arg Gln Ser Tyr Gly Gly Gly Phe Arg Tyr Ser Gln
            195                 200                 205

Ala Glu Ala Phe Ser Pro Thr Ala Asn Met Ala Pro Pro Met Pro
210                 215                 220

Thr Thr Gly Leu Ala Ala Gly Val Val Val Asp His Leu Leu Pro Leu
225                 230                 235                 240

Glu Pro Arg Asp Ile Pro Phe Asp Val Cys Asp Leu His Asp Ala Lys
                245                 250                 255

Ser Pro Met Ser Lys Phe Glu Asn Leu Pro Ala Val Leu Arg Tyr Arg
                260                 265                 270

Ala Arg Ser His Pro Lys Gln Pro Ala Tyr Trp Val Leu Asp Gln Arg
            275                 280                 285

Gly Lys Glu Thr Ala Ser Ile Thr Trp Glu Lys Leu Ala Ser Arg Ala
    290                 295                 300

Glu Lys Val Ala Gln Val Ile Arg Asp Lys Ser Ser Leu Tyr Arg Gly
305                 310                 315                 320

Asp Arg Val Ala Leu Val Tyr Arg Asp Thr Glu Val Ile Glu Phe Ala
                325                 330                 335

Val Ala Leu Leu Gly Cys Phe Ile Ala Gly Val Val Ala Val Pro Ile
            340                 345                 350

Asn Asn Leu Asp Asp Tyr Ala Ser Leu Asn Val Ile Leu Thr Ser Thr
            355                 360                 365

Gln Ala His Leu Ala Leu Thr Thr Glu Asn Asn Leu Lys Ala Phe Gln
    370                 375                 380

Arg Asp Ile Ala Thr Gln Lys Leu Thr Trp Pro Arg Gly Val Glu Trp
385                 390                 395                 400

Trp Lys Thr Asn Glu Phe Gly Ser Tyr His Pro Lys Arg Lys Asp Glu
                405                 410                 415

Met Pro Pro Leu Ala Val Pro Asp Leu Ala Tyr Ile Glu Phe Ala Arg
            420                 425                 430

Ala Pro Thr Gly Asp Leu Arg Gly Val Val Met Ser His Arg Thr Ile
            435                 440                 445
```

-continued

Met His Gln Met Cys Cys Met Ser Ala Ile Val Ser Thr Ile Pro Thr
450                 455                 460

Asp Ser Asn Asn Ser Gly Lys Pro Val Pro Arg Pro His Gly Glu Ile
465                 470                 475                 480

Leu Met Ser Tyr Leu Asp Pro Arg Gln Gly Ile Gly Met Ile Leu Gly
            485                 490                 495

Val Leu Phe Thr Val Tyr Ala Gly Asn Thr Thr Val Trp Leu Glu Ser
            500                 505                 510

Leu Ala Val Glu Thr Pro Gly Leu Tyr Ala Ser Leu Ile Thr Lys Tyr
            515                 520                 525

Arg Ala Ala Leu Leu Ala Ala Asp Tyr Pro Gly Leu Lys Arg Ala Val
530                 535                 540

Tyr Asn Tyr Gln Gln Asp Pro Met Ala Thr Arg Asn Phe Lys Lys Asn
545                 550                 555                 560

Ser Glu Pro Asn Phe Ser Ser Leu Lys Leu Cys Leu Ile Asp Thr Leu
                565                 570                 575

Thr Val Asp Cys Glu Phe His Glu Ile Leu Ala Asp Arg Trp Leu Arg
            580                 585                 590

Pro Leu Arg Asn Pro Arg Ala Arg Glu Leu Val Thr Pro Met Leu Cys
            595                 600                 605

Leu Pro Glu His Gly Gly Met Val Ile Ser Leu Arg Asp Trp Leu Gly
610                 615                 620

Gly Glu Glu Arg Met Gly Cys Pro Leu Lys His Glu Val Leu Pro Pro
625                 630                 635                 640

Glu Lys Gln Lys Asp Lys Ser Glu Gly Glu Lys Lys Glu Glu Glu Lys
            645                 650                 655

Gly Gly Glu Pro Lys Ala Thr Phe Gly Ser Ser Leu Ile Gly Gly Ser
            660                 665                 670

Ala Ala Pro Val Arg Lys Glu Gly Pro Arg Asn Asp Leu Gly Glu Val
            675                 680                 685

Leu Leu Asp Lys Glu Ala Leu Lys Asn Asn Glu Ile Val Ile Leu Ala
            690                 695                 700

Ile Gly Glu Glu Ala Arg Arg Leu Ala Asp Thr Thr Pro Asn Ala Val
705                 710                 715                 720

Arg Ile Gly Ala Phe Gly Tyr Pro Ile Pro Asp Ala Thr Leu Ala Ile
            725                 730                 735

Val Asp Pro Glu Thr Gly Leu Leu Cys Thr Pro Asn Val Val Gly Glu
            740                 745                 750

Ile Trp Val Asp Ser Pro Ser Leu Ser Gly Gly Phe Trp Ala Leu Pro
            755                 760                 765

Lys Gln Thr Glu Ser Ile Phe His Ala Arg Pro Tyr Arg Phe Gln Gly
            770                 775                 780

Gly Gly Pro Thr Pro Val Ile Val Glu Pro Glu Phe Leu Arg Thr Gly
785                 790                 795                 800

Leu Leu Gly Cys Val Ile Glu Gly Gln Ile Phe Val Leu Gly Leu Tyr
            805                 810                 815

Glu Asp Arg Leu Arg Gln Lys Val Glu Trp Gly Glu His Gly Val Glu
            820                 825                 830

Val Ala Glu His Arg Tyr Phe Phe Val Gln His Leu Ile Leu Ser Ile
            835                 840                 845

Met Lys Asn Val Pro Lys Ile His Asp Cys Ser Ala Phe Asp Val Phe
850                 855                 860

Val Asn Glu Glu His Leu Pro Val Val Val Leu Glu Ser Tyr Thr Ala

```
                865                 870                 875                 880
Ser Thr Ala Pro Val Ala Ser Gly Gln Ser Pro Arg Gln Leu Asp Val
                    885                 890                 895

Pro Leu Leu Asp Ser Leu Ala Glu Lys Cys Met Gly Val Leu Tyr Gln
                900                 905                 910

Glu His His Leu Arg Val Tyr Cys Val Met Ile Thr Ala Pro Asn Thr
                915                 920                 925

Leu Pro Arg Val Leu Lys Asn Gly Arg Gln Glu Ile Gly Asn Met Leu
            930                 935                 940

Cys Arg Lys Glu Phe Asp Asn Gly Ser Leu Pro Cys Glu His Val Lys
945                 950                 955                 960

Phe Ser Val Glu Arg Ser Val Leu Asn Leu Pro Ile Gly Val Asp Pro
                965                 970                 975

Val Gly Gly Ile Trp Ser Val Pro Ser Ser Ala Ala Arg Gln Asp Ala
            980                 985                 990

Leu Ala Met Gln Glu Lys Gln Tyr Ser Gly Val Asp Leu Arg Asp Val
                995                 1000                1005

Ile Met Asp Asp Arg Thr Ser Thr Pro Leu Asn Asn Phe Asn Ser
    1010                1015                1020

Ile Val Asp Leu Leu Gln Trp Arg Val Ser Arg Gln Gly Glu Glu
    1025                1030                1035

Leu Cys Tyr Cys Ser Ile Asp Gly Arg Gly Arg Glu Gly Lys Gly
    1040                1045                1050

Ile Thr Trp Lys Lys Phe Asp Ser Lys Val Ala Ala Val Ala Ala
    1055                1060                1065

Tyr Leu Lys Asn Lys Val Lys Leu Arg Pro Gly Asp His Val Ile
    1070                1075                1080

Leu Met Tyr Thr His Ser Glu Glu Tyr Val Phe Ala Val His Ala
    1085                1090                1095

Cys Phe Cys Leu Gly Leu Val Ala Ile Pro Ile Ser Pro Val Asp
    1100                1105                1110

Gln Asn Arg Leu Ser Glu Asp Ala Pro Ala Leu Leu His Val Ile
    1115                1120                1125

Val Asp Phe Arg Val Lys Ala Ile Leu Val Asn Gly Glu Val Asn
    1130                1135                1140

Asp Leu Leu Lys Gln Lys Ile Val Ser Gln His Ile Lys Gln Ser
    1145                1150                1155

Ala His Val Val Arg Thr Ser Val Pro Ser Val Tyr Asn Thr Ser
    1160                1165                1170

Lys Pro Pro Lys Gln Ser His Gly Cys Arg His Leu Gly Phe Thr
    1175                1180                1185

Met Asn Pro Gln Trp Leu Asn Ser Lys Gln Pro Ala Val Ile Trp
    1190                1195                1200

Thr Tyr Trp Thr Pro Asp Gln Arg Arg Leu Ser Val Glu Ile Gly
    1205                1210                1215

His Asp Thr Ile Met Gly Met Cys Lys Val Gln Lys Glu Thr Cys
    1220                1225                1230

Gln Met Ser Ser Ser Arg Pro Val Leu Gly Ser Val Arg Ser Ala
    1235                1240                1245

Val Gly Leu Gly Phe Leu His Thr Cys Leu Met Gly Pro Tyr Val
    1250                1255                1260

Gly Ala Pro Thr Tyr Leu Val Ser Pro Ile Asp Phe Ala Ala Asn
    1265                1270                1275
```

-continued

Pro Ile Ser Leu Phe Leu Thr  Leu Ala Arg Tyr Lys  Ile Lys Asp
    1280             1285              1290

Thr Tyr Ala Thr Ser Gln Met  Leu Asp Tyr Ala Met  Gly Ser Met
    1295             1300              1305

Ala Ala Lys Gly Phe Gln Leu  His Glu Leu Lys Asn  Leu Met Ile
    1310             1315              1320

Ser Ala Glu Gly Arg Pro Arg  Ile Asp Val Tyr Gln  Lys Val Arg
    1325             1330              1335

Leu His Phe Ala Ala Ala Gly  Leu Asp Arg Thr Ala  Ile Asn Thr
    1340             1345              1350

Ile Tyr Ser His Val Leu Asn  Pro Met Ile Ala Ser  Arg Ser Tyr
    1355             1360              1365

Met Cys Ile Glu Pro Ile Glu  Leu Trp Leu Asp Thr  Lys Tyr Leu
    1370             1375              1380

Arg Gln Gly Tyr Val Tyr Pro  Val Asp Pro Asp Thr  Pro Gly His
    1385             1390              1395

Thr Leu Leu Val Gln Asp Ser  Gly Met Val Pro Val  Ser Thr Gln
    1400             1405              1410

Ile Ala Ile Val Asn Pro Glu  Thr Cys Cys Leu Ser  His Val Gly
    1415             1420              1425

Glu Tyr Gly Glu Ile Trp Val  Gln Ser Asp Ala Cys  Ala Arg Ser
    1430             1435              1440

Phe Tyr Gly Ser Lys Gln Glu  Phe Asp Leu Glu Arg  Phe Asn Gly
    1445             1450              1455

Arg Thr Val Asp Gly Asp Pro  Gly Ala Ile Tyr Val  Arg Thr Gly
    1460             1465              1470

Asp Leu Gly Phe Leu His Thr  Val Thr Arg Pro Ile  Gly Pro Gly
    1475             1480              1485

Gly Gln Pro Val Glu Met Gln  Val Leu Phe Val Leu  Gly Ser Ile
    1490             1495              1500

Gly Glu Thr Phe Glu Val Asn  Gly Leu Asn His Phe  Pro Met Asp
    1505             1510              1515

Ile Glu Asn Thr Ile Glu Lys  Ser His Arg Asn Ile  Val Arg Gly
    1520             1525              1530

Gly Ser Ala Val Phe Gln Ala  Gly Gly Leu Val Val  Ala Leu Val
    1535             1540              1545

Glu Val Thr Arg Lys Ala Tyr  Leu Ala Ser Ile Val  Pro Val Ile
    1550             1555              1560

Val Asn Ala Val Leu Thr Glu  His Gln Val Val Thr  Asp Ile Val
    1565             1570              1575

Ala Phe Val Pro Arg Gly Asp  Phe Pro Arg Ser Arg  Leu Gly Glu
    1580             1585              1590

Lys Gln Arg Gly Lys Ile Leu  Gly Leu Trp Val Thr  Arg Lys Ile
    1595             1600              1605

Arg Thr Ile Ala Gln Phe Ser  Ile Arg Asp Ala Asp  Gly Val Met
    1610             1615              1620

Thr His Val Ala Glu Ala His  Ala Arg Ala Ser Lys  Thr Gly Ser
    1625             1630              1635

Ile Ile Glu Gly Ser Gly Arg  Leu Pro Ser Thr Leu  Leu Glu Ala
    1640             1645              1650

Glu Glu His Gly Gly Pro Gln  Pro Gln Ala Pro Ser  Arg Arg Gly
    1655             1660              1665

-continued

```
Lys Gly Tyr Thr Asp Glu Pro Val Glu His Tyr Pro Arg Thr Pro
    1670                1675                1680

Glu Gly Ile Ile Ser Asp His His Ala Leu Gly Asp Pro Thr Phe
    1685                1690                1695

Arg Asn Ala Asp Asp Thr Glu Gln Tyr His Gln Ser Phe Lys His
    1700                1705                1710

Asp Asn Arg Ser Ser Ser Gly Asn Phe Tyr Asp Gln Asn Gln Asp
    1715                1720                1725

Glu Arg His Asp Phe Leu Val Glu Ser Pro Met Ala Ala Glu Asn
    1730                1735                1740

Gly Ser Ala Pro Phe Asn Ala Ser Ala Phe Gly Ser Gln Gly Ser
    1745                1750                1755

Asn Phe Ala Pro Glu Asn His Pro Leu Gln Gly Glu Cys Asn Pro
    1760                1765                1770

Ser Gly Pro Ile Gly Leu Val Pro Met Lys Pro Leu Ser Arg Gln
    1775                1780                1785

Asp Thr Pro Pro Ser His Arg Ser Ser Ser Arg Ser Ser Pro Ala
    1790                1795                1800

Pro Gln Thr Val Pro Arg Ile Arg Thr Pro Val Met Thr Leu Gly
    1805                1810                1815

Lys Asp Ser Leu Pro Ser Gln Gln Leu Arg Tyr Ser Met Ile Gly
    1820                1825                1830

Gly Ser Tyr Asn Gln Pro Pro Pro Gln Gln Ala Gln Thr Gln Gly
    1835                1840                1845

Gln Asn Pro Tyr Gly Gly Tyr Gly Asp Glu His Glu Gln Asp Trp
    1850                1855                1860

Pro Gln Glu Ala Ile Leu Tyr His Thr Arg Asn Asp Ala Gly Tyr
    1865                1870                1875

Gln

```
<210> SEQ ID NO 2
<211> LENGTH: 6461
<212> TYPE: DNA
<213> ORGANISM: Coccidioides immitis

<400> SEQUENCE: 2

```
catcgtcatg atcccgaaaa tgcacccatg atccttggat tgggctgagg actgaagacg      60
cttttaatct cctggagttc atttcaagta cgaactgaca tgtggcgcaa ccgcgaaacg     120
acgatactga ttggcgttta acatggctga agagaatccc gagctccagg ccgccttgcg     180
ggaacttgat caggaactgg aggtgtgtgc aacctttgac ttgtattcga cagagactgc     240
ttttctgaaa tgaatagaag cgctgacggg atgctattct aggacggtga tatcacagag     300
aaagggtaag cagccggact tgtcaacacc tgcctatact cgcgcgcggt cagattttgc     360
attcgagccg agcagacccg agcggagtcg cgtggggaac ttagatttat taactgctat     420
taagatatca gaagcgtcgg acactcctcc tttcgcagta tctttctgcg gatggagccc     480
agggaaatca agagcttcga tttatgcgac ggccctcgca cgatgctcct accacgatag     540
caggcggaca ggtcaaccgc aggtcagtgt atgcggataa ccggcggcaa tctgactatc     600
ttcctgcaaa cctcctctct ccagcagaca gtggctatac cgatccgcgt gcgaacccgt     660
tatcgagaat ccatgaaaat gaactgggtt tctcactcaa tccgactcag cagccatcga     720
ggacttcgta tgattcaatg caagctccaa tggccaatcc ctccgtcgcg gattacgatc     780
attctcggtc gccaacggta ataagccaaa attatgcatt caatccgaac gagcaaccgg     840
```

```
aatatgatag tctcacaaga aattccacga tgctagactc ccaggaagcg tacttttcag    900
actttgcagg tgagcagcat gatgagcgga gacagagtta cggtggtgga ttccggtatt    960
cccaagccga agcgttctca cccacggcca atatggcgcc gccccaatg cccacaacgg   1020 gcctggctgc aggggtagtg gtcgaccatc ttttaccatt ggaaccacgg gatattccct   1080
tcgacgtttg tgaccttcat gatgccaagt ctccaatgtc taaatttgaa aatttgcctg   1140
cagtgctacg ttaccgtgca cgctcccacc cgaagcagcc agcctactgg gtactcgacc   1200
agcggggtaa ggagacggca tcgataactt gggagaagct tgccagccgt gcggagaagg   1260
ttgctcaagt gatccgtgac aagagcagtc tataccgtgg tgatcgcgtt gccctagttt   1320
atcgcgatac cgaagttatc gaatttgcgg tggcattgct tgggtgtttc atcgctggag   1380
tagtcgccgt tcccattaac aacctcgacg attatgctag tctcaatgtc atcctcacat   1440
cgactcaagc ccatcttgcc ctgacaacgg agaataattt aaaagcgttc cagcgcgata   1500
tcgcaaccca aaaattaacg tggccaagag gggttgaatg gtggaagaca aacgagtttg   1560
gtagctatca ccctaagcga aaggatgaga tgcccccct agccgtcccg gatttggcat   1620
acatcgagtt tgcgagggct cccactggcg atttgcgggg agtggtgatg agccaccgca   1680
ccatcatgca tcaaatgtgc tgcatgtctg cgatagtatc tacgattccc accgattcca   1740
ataatagcgg gaaacctgtg ccaagacctc acggcgaaat cctgatgagt tatctcgatc   1800
ctagacaagg cattggcatg atccttggtg ttctctttac ggtctatgct ggcaatacta   1860
ctgtttggct agagtcccta gcggttgaaa ctccccggcct ttatgctagt ttgatcacca   1920
agtacagagc tgctctgctg gctgcagatt acccgggcct taagagggcc gtgtacaatt   1980
accagcaaga tccgatggcg acaagaaatt caagaagaa ttcagagcca aacttctcaa   2040
gcttgaagtt gtgtcttata gatactttaa ctgtcgactg cgaattccat gaaatcctcg   2100
ctgacagatg gttaaggccc ttgcggaatc cgcgggctcg cgaactagtt acgcccatgc   2160
tgtgccttcc agagcacggt ggcatggtta tcagtttacg tgactggctt ggaggcgagg   2220
agcgtatggg gtgcccttg aaacatgaag tactgccacc ggaaaagcag aaagacaagt   2280
ccgaaggtga gaaaaagaa gaagagaagg gcggagagcc aaaggcgacg ttcgggagca   2340
gcttgattgg tggttctgcg gcaccggtac gaaaagaagg cccccggaac gaccttggtg   2400
aggtactact tgacaaagaa gccttgaaaa acaacgaaat tgtgatatta gcaattggtg   2460
aggaggcaag aaggctggct gacacaacac caaatgctgt caggattggt gcatttgggt   2520
atcccattcc agatgcaacc ttagcgatcg ttgatccaga gactgggttg ctgtgcacgc   2580
ctaatgtggt tggtgagata tgggttgatt caccttcatt gtcaggagga ttctgggccc   2640
ttcctaaaca aacggagtcc atcttccatg cccgtcccta ccgatttcag ggaggggtc   2700 ccacgcctgt aatcgtggag cctgaattct tgcgaacagg gcttcttggc tgtgttattg   2760
agggtcaaat attcgtgctt ggtctctacg aagatcgctt gcgccaaaaa gttgaatggg   2820
gtgagcatgg cgtagaagtt gcggagcacc gatatttctt cgtgcaacat ctgattctca   2880
gtattatgaa gaacgtgccc aaaattcacg actgctctgc ctttgacgtc ttcgtcaacg   2940
aggagcacct gccagtcgtt gtcttggagt cgtatactgc ctcaacagca ccagtagctt   3000
cagggcaatc cccacgacag ctggacgttc ctcttttgga ctccttggct gagaaatgca   3060
tgggagtgct ataccaagaa catcaccttc gcgtttattg tgtcatgatc actgccccga   3120
ataccttgcc tagagttctt aaaaatgggc gccaagagat tggcaacatg ctatgtcgaa   3180
```

```
aagaatttga taatgggtcg ctgccatgcg agcacgttaa attcagcgtt gagcggtcgg   3240
ttctgaatct tccaattggc gtggatcccg ttggaggaat ttggtctgtt ccatcttcag   3300
ctgctaggca ggatgccctc gccatgcagg aaaagcaata ttcaggagtt gatttgcgcg   3360
acgttattat ggatgatcgc acctctacgc cattgaataa ttttaacagt atcgttgatt   3420
tacttcagtg gcgtgtttct cgccagggcg aggaactttg ttattgctct atcgacggtc   3480
gtggcagaga aggcaagggt atcacatgga agaaattcga ttctaaagtt gcagctgtgg   3540
ctgcgtattt gaaaaataaa gtgaaactcc gccccggcga ccatgttatt ctcatgtata   3600
cgcactcgga agagtacgta ttcgccgtac atgcttgctt ctgcctgggt ttggtagcca   3660
ttcccatttc cccagttgac cagaaccgac tatccgaaga tgcgccggct ttactccatg   3720
tcattgtcga tttccgtgta aaagccatac ttgtcaacgg cgaagtcaat gacttactga   3780
aacagaaaat cgtatctcag catatcaagc agtctgctca tgttgtccgc acgagcgttc   3840
caagtgtata caatacgtcg aagccccaa agcaatcgca cggttgccgc catctaggat   3900
ttactatgaa tccccaatgg ttgaattcta agcagccagc agtgatttgg acgtactgga   3960
ctccggatca acgaagactg tctgtcgaga tcgggcatga tacaatcatg ggaatgtgca   4020
aggtccaaaa ggaaacctgc caaatgtcta gttcacggcc agttttggga agtgtgcgca   4080
gtgctgtagg ccttgggttt ctacacacct gcttgatggg ccctacgtc ggtatgtttt   4140
cggcctgtgt ttttgaaagt gtcctggatt aagcttacat atttccaggc gcacccactt   4200
accttgtttc gcccattgat tttgctgcga acccaatttc tttgttcctg accctagcga   4260
gatataaaat caaggatacc tacgcaacta gccaaatgtt ggactacgca atggggagca   4320
tggctgcaaa gggcttttcaa ttgcatgaat tgaaaaatct catgatttcc gcggaaggac   4380
gacctagaat cgacgtttgt atgttttgag gtattgatca cgtcgggaaa tttgacaagc   4440
taattattct gttagaccaa aaagtgcgct tacatttcgc tgccgctggg ctcgatcgta   4500
ccgctatcaa tactatttac tctcatgtcc tgaatcctat gattgcctcc cgatcataca   4560
tgtgcattga accgatcgaa ctgtggcttg atacaaaata tcttagacag gctacgtttt   4620
atccggtgga tccggatact cctggacata cgcttttagt tcaagactca gggatggttc   4680
ctgtgagcac gcaaatagcc atagtgaatc cagagacttg ttgcctttct catgttggcg   4740
aatatggcga aatatgggtt caatccgatg cctgtgccag gtccttctat ggctctaagc   4800
aggaattcga cctagagagg ttcaatggac gaactgtgga tggcgatcca ggtgccatat   4860
atgttcgtac tggtgattta ggtttcttac atacagtgac gaggccgatt ggacctggtg   4920
ggcaaccagt cgaaatgcag gttctgtttg tcttgggtag catcggtgaa accttgaag   4980
tcaatggtct caaccatttc cctatggaca ttgagaacac aattgagaag tcacatcgaa   5040
atatagttag gggaggaagg tcagtgaatc catccattgc tcaatttct aatctctttt   5100
gctgacgtct gacaaacagc gccgtattcc aagctggtgg gctagttgtt gctcttgttg   5160
aagttacccg aaaagcctat cttgcatcca ttgtacctgt gattgtgaat gcagttctta   5220
ctgagcatca ggtcgtcact gacattgtcg ccttcgttcc tcgtggtgac ttccctcgtt   5280
cacgcctggg tgagaagcaa cgcggcaaga ttcttggatt gtgggttact cggaagatcc   5340
ggacgattgc acaatttagc atcagggatg cggatggagt gatgacccat gtcgcagagg   5400
cccatgcaag ggcgtcaaaa accggaagta ttattgaagg aagtggtcgc ctaccttcta   5460
cgctcctgga agcagaggaa catggaggac ctcagccgca ggctccgtcg aggcgcggca   5520
agggatatac agatgaacct gttgagcatt atccccgtac ccctgaaggt attatatcgg   5580
```

```
atcaccatgc cctcggagat ccaacattta gaaatgcaga tgacactgag cagtaccatc    5640
agtcttttaa gcacgataat cgcagctctt ctggcaattt ctatgaccaa aaccaggatg    5700
aacgacacga tttcttggta gagtctccta tggccgctga aaacggatcc gctcccttca    5760
atgccagcgc tttcggctct caaggctcaa actttgctcc tgagaatcac cctctccagg    5820
gcgaatgtaa cccatctggt cccataggtc tagtccccat gaaacctctc tcacggcagg    5880
atactcctcc gtctcatcga tctagttctc gctcctctcc agctcacag accgtccccc    5940 ggatccggac tcccgtaatg acacttggaa aagattcttt acccagtcaa caactaagat    6000
acagcatgat tggaggctcc tacaaccaac cccctcccca gcaagctcag actcaaggcc    6060
agaatccgta tggcggctac ggtgatgagc acgagcagga ttggccacag gaggcgatcc    6120
tttaccatac aaggaatgat gcgggatatc aatagacaca tgaggattgc tcggctttgt    6180
cttttctctt ctttcccctt ttttttaat ttgtaaggtc ctggaatatg gcttgcttgg    6240
gttctgtcag cttcgggaaa ggttcgaatt ttctcatcga tcagcagcat cctggcgttg    6300
gcatgaatca catttccttg atttggtgac gccggatatc ccccaaacag ccacgtgcat    6360
ttatgatata actagttaat ggttttttttt ataattatag tgcaatgtta tagacatacc    6420
ttttgtgtat ccatggagaa gtaagatact aggtcaaaag t                        6461
```

<210> SEQ ID NO 3
<211> LENGTH: 5640
<212> TYPE: DNA
<213> ORGANISM: Coccidioides immitis

<400> SEQUENCE: 3
atggctgaag agaatcccga gctccaggcc gccttgcggg aacttgatca ggaactggag 60
gacggtgata tcacagagaa aggatatcag aagcgtcgga cactcctcct ttcgcagtat 120
ctttctgcgg atggagccca gggaaatcaa gagcttcgat ttatgcgacg gccctcgcac 180
gatgctccta ccacgatagc aggcggacag gtcaaccgca ggtcagtgta tgcggataac 240
cggcggcaat ctgactatct tcctgcaaac ctcctctctc cagcagacag tggctatacc 300
gatccgcgtg cgaacccgtt atcgagaatc catgaaaatg aactgggttt ctcactcaat 360
ccgactcagc agccatcgag gacttcgtat gattcaatgc aagctccaat ggccaatccc 420
tccgtcgcgg attacgatca ttctcggtcg ccaacggtaa taagccaaaa ttatgcattc 480
aatccgaacg agcaaccgga atatgatagt ctcacaagaa attccacgat gctagactcc 540
caggaagcgt acttttcaga ctttgcaggt gagcagcatg atgagcggag acagagttac 600
ggtggtggat tccggtattc ccaagccgaa gcgttctcac ccacggccaa tatggcgccg 660
cccccaatgc ccacaacggg cctggctgca ggggtagtgg tcgaccatct tttaccattg 720
gaaccacggg atattccctt cgacgtttgt gaccttcatg atgccaagtc tccaatgtct 780
aaatttgaaa atttgcctgc agtgctacgt taccgtgcac gctcccaccc gaagcagcca 840
gcctactggg tactcgacca gcggggtaag gagacggcat cgataacttg ggagaagctt 900
gccagccgtg cggagaaggt tgctcaagtg atccgtgaca agagcagtct ataccgtggt 960
gatcgcgttg ccctagttta tcgcgatacc gaagttatcg aatttgcggt ggcattgctt 1020
gggtgtttca tcgctggagt agtcgccgtt cccattaaca acctcgacga ttatgctagt 1080
ctcaatgtca tcctcacatc gactcaagcc catcttgccc tgacaacgga gaataattta 1140
aaagcgttcc agcgcgatat cgcaacccaa aaattaacgt ggccaagagg ggttgaatgg 1200

```
tggaagacaa acgagtttgg tagctatcac cctaagcgaa aggatgagat gccccccta      1260 gccgtcccgg atttggcata catcgagttt gcgagggctc ccactggcga tttgcgggga      1320
gtggtgatga gccaccgcac catcatgcat caaatgtgct gcatgtctgc gatagtatct      1380
acgattccca ccgattccaa taatagcggg aaacctgtgc caagacctca cggcgaaatc      1440
ctgatgagtt atctcgatcc tagacaaggc attggcatga tccttggtgt tctctttacg      1500
gtctatgctg gcaatactac tgtttggcta gagtccctag cggttgaaac tcccggcctt      1560
tatgctagtt tgatcaccaa gtacagagct gctctgctgg ctgcagatta cccgggcctt      1620
aagagggccg tgtacaatta ccagcaagat ccgatggcga caagaaattt caagaagaat      1680
tcagagccaa acttctcaag cttgaagttg tgtcttatag atactttaac tgtcgactgc      1740
gaattccatg aaatcctcgc tgacagatgg ttaaggccct tgcggaatcc gcgggctcgc      1800
gaactagtta cgcccatgct gtgccttcca gagcacggtg gcatggttat cagtttacgt      1860
gactggcttg gaggcgagga gcgtatgggg tgccctttga acatgaagt actgccaccg       1920 gaaaagcaga aagacaagtc cgaaggtgag aaaaaagaag aagagaaggg cggagagcca      1980
aaggcgacgt tcgggagcag cttgattggt ggttctgcgg caccggtacg aaaagaaggc      2040 cccggaacg accttggtga ggtactactt gacaaagaag ccttgaaaaa caacgaaatt       2100
gtgatattag caattggtga ggaggcaaga aggctggctg acacaacacc aaatgctgtc      2160
aggattggtg catttgggta tcccattcca gatgcaacct tagcgatcgt tgatccagag      2220
actgggttgc tgtgcacgcc taatgtggtt ggtgagatat gggttgattc accttcattg      2280
tcaggaggat tctgggccct tcctaaacaa acggagtcca tcttccatgc ccgtccctac      2340
cgatttcagg agggggtcc cacgcctgta atcgtggagc ctgaattctt gcgaacaggg       2400
cttcttggct gtgttattga gggtcaaata ttcgtgcttg gtctctacga agatcgcttg      2460
cgccaaaaag ttgaatgggg tgagcatggc gtagaagttg cggagcaccg atatttcttc      2520
gtgcaacatc tgattctcag tattatgaag aacgtgccca aaattcacga ctgctctgcc      2580
tttgacgtct tcgtcaacga ggagcacctg ccagtcgttg tcttggagtc gtatactgcc      2640
tcaacagcac cagtagcttc agggcaatcc ccacgacagc tggacgttcc tcttttggac      2700
tccttggctg agaaatgcat gggagtgcta taccaagaac atcaccttcg cgtttattgt      2760
gtcatgatca ctgccccgaa taccttgcct agagttctta aaaatgggcg ccaagagatt      2820
ggcaacatgc tatgtcgaaa agaatttgat aatgggtcgc tgccatgcga gcacgttaaa      2880
ttcagcgttg agcggtcggt tctgaatctt ccaattggcg tggatcccgt tggaggaatt      2940
tggtctgttc catcttcagc tgctaggcag gatgccctcg ccatgcagga aaagcaatat      3000
tcaggagttg atttgcgcga cgttattatg gatgatcgca cctctacgcc attgaataat      3060
tttaacagta tcgttgattt acttcagtgg cgtgtttctc gccagggcga ggaactttgt      3120
tattgctcta tcgacggtcg tggcagagaa ggcaagggta tcacatggaa gaaattcgat      3180
tctaaagttg cagctgtggc tgcgtatttg aaaaataaag tgaaactccg ccccggcgac      3240
catgttattc tcatgtatac gcactcggaa gagtacgtat tcgccgtaca tgcttgcttc      3300 tgcctggggtt tggtagccat tcccatttcc ccagttgacc agaaccgact atccgaagat      3360
gcgccggctt tactccatgt cattgtcgat ttccgtgtaa aagccatact tgtcaacggc      3420
gaagtcaatg acttactgaa acagaaaatc gtatctcagc atatcaagca gtctgctcat      3480
gttgtccgca cgagcgttcc aagtgtatac aatacgtcga agcccccaaa gcaatcgcac      3540
ggttgccgcc atctaggatt tactatgaat ccccaatggt tgaattctaa gcagccagca      3600
```

```
gtgatttgga cgtactggac tccggatcaa cgaagactgt ctgtcgagat cgggcatgat    3660
acaatcatgg gaatgtgcaa ggtccaaaag gaaacctgcc aaatgtctag ttcacggcca    3720
gttttgggaa gtgtgcgcag tgctgtaggc cttgggtttc tacacacctg cttgatgggg    3780
ccctacgtcg gcgcacccac ttaccttgtt tcgcccattg attttgctgc gaacccaatt    3840
tctttgttcc tgaccctagc gagatataaa atcaaggata cctacgcaac tagccaaatg    3900
ttggactacg caatggggag catggctgca aagggctttc aattgcatga attgaaaaat    3960
ctcatgattt ccgcggaagg acgacctaga atcgacgttt accaaaaagt gcgcttacat    4020
ttcgctgccg ctgggctcga tcgtaccgct atcaatacta tttactctca tgtcctgaat    4080
cctatgattg cctcccgatc atacatgtgc attgaaccga tcgaactgtg gcttgataca    4140
aaatatctta gacagggcta cgtttatccg gtgatccgg  atactcctgg acatacgctt    4200
ttagttcaag actcagggat ggttcctgtg agcacgcaaa tagccatagt gaatccagag    4260
acttgttgcc tttctcatgt tggcgaatat ggcgaaatat gggttcaatc cgatgcctgt    4320
gccaggtcct tctatggctc taagcaggaa ttcgacctag agaggttcaa tggacgaact    4380
gtggatggcg atccaggtgc catatatgtt cgtactggtg atttaggttt cttacataca    4440
gtgacgaggc cgattggacc tggtgggcaa ccagtcgaaa tgcaggttct gtttgtcttg    4500
ggtagcatcg gtgaaacctt tgaagtcaat ggtctcaacc atttccctat ggacattgag    4560
aacacaattg agaagtcaca tcgaaatata gttaggggag gaagcgccgt attccaagct    4620
ggtgggctag ttgttgctct tgttgaagtt acccgaaaag cctatcttgc atccattgta    4680
cctgtgattg tgaatgcagt tcttactgag catcaggtcg tcactgacat tgtcgccttc    4740
gttcctcgtg gtgacttccc tcgttcacgc ctgggtgaga agcaacgcgg caagattctt    4800
ggattgtggg ttactcggaa gatccggacg attgcacaat ttagcatcag ggatgcggat    4860
ggagtgatga cccatgtcgc agaggcccat gcaagggcgt caaaaaccgg aagtattatt    4920
gaaggaagtg gtcgcctacc ttctacgctc ctggaagcag aggaacatgg aggacctcag    4980
ccgcaggctc cgtcgaggcg cggcaaggga tatacagatg aacctgttga gcattatccc    5040 cgtaccctg  aaggtattat atcggatcac catgccctcg gagatccaac atttagaaat    5100
gcagatgaca ctgagcagta ccatcagtct tttaagcacg ataatcgcag ctcttctggc    5160
aatttctatg accaaaaacca ggatgaacga cacgatttct tggtagagtc tcctatggcc    5220
gctgaaaacg gatccgctcc cttcaatgcc agcgctttcg gctctcaagg ctcaaacttt    5280
gctcctgaga atcaccctct ccagggcgaa tgtaacccat ctggtcccat aggtctagtc    5340
cccatgaaac ctctctcacg gcaggatact cctccgtctc atcgatctag ttctcgctcc    5400
tctccagctc cacagaccgt cccccggatc cggactcccg taatgacact tggaaaagat    5460
tctttaccca gtcaacaact aagatacagc atgattggag ctcctacaa  ccaacccccct    5520 ccccagcaag ctcagactca aggccagaat ccgtatggcg gctacggtga tgagcacgag    5580
caggattggc cacaggaggc gatcctttac catacaagga atgatgcggg atatcaatag    5640
```

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4

```
gtgggtatca gttgtttgta ggaag                                         25

<210> SEQ ID NO 5
<211> LENGTH: 55
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gctccttcaa tatcagttaa cgtcgagtta aacgccaatc agtatcgtcg tttcg        55

<210> SEQ ID NO 6
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
agatgccgac cgggaaccag ttaacataga catgaggatt gctcggcttt gtc          53

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tcacgatgtc gtacgggcca gtttg                                         25

<210> SEQ ID NO 8
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gggaattcga attcgcgtgg tctggtagtc gcgttgagag cc                      42

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gagccggaat tccctaaatg catagccatt ccacaaatac                         40

<210> SEQ ID NO 10
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 10
caaccgcagg tcagtgtatg                                                   20
```